United States Patent
Sher-Jan et al.

(10) Patent No.: US 10,204,238 B2
(45) Date of Patent: *Feb. 12, 2019

(54) SYSTEMS AND METHODS FOR MANAGING DATA INCIDENTS

(71) Applicant: RADAR, Inc., Portland, OR (US)

(72) Inventors: Mahmood Sher-Jan, Lake Oswego, OR (US); Kelly Burg, Scappoose, OR (US); Nicholas J. Church, Milwaukie, OR (US); Reno Brown, Portland, OR (US); Tim Garton, Beaverton, OR (US); Andrew Migliore, Portland, OR (US)

(73) Assignee: RADAR, Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,786

(22) Filed: Oct. 31, 2016

(65) Prior Publication Data

US 2017/0206376 A1 Jul. 20, 2017

Related U.S. Application Data

(63) Continuation-in-part of application No. 14/868,311, filed on Sep. 28, 2015, now Pat. No. 9,781,147, which
(Continued)

(51) Int. Cl.
*G06F 21/62* (2013.01)
*H04L 29/06* (2006.01)
(Continued)

(52) U.S. Cl.
CPC ........ *G06F 21/6245* (2013.01); *G06F 21/577* (2013.01); *G06F 21/60* (2013.01);
(Continued)

(58) Field of Classification Search
CPC .... G06F 21/6245; G06F 21/577; G06F 21/60; G06F 19/322; H04L 63/1433; H04L 29/06904
(Continued)

(56) References Cited

U.S. PATENT DOCUMENTS 6,148,297 A * 11/2000 Swor ............... G06F 19/324
6,901,372 B1  5/2005 Helzerman
(Continued)

OTHER PUBLICATIONS

European Commission, "Proposal for a Regulation of the European Parliament and of the Council on the protection of individuals with regard to the processing of personal data and on the free movement of such data (General Data Protection Regulation)", Jan. 25, 2012,European Commission, Brussels, Jan. 25, 2012, COM(2012) 11 final, 2012/0011 (COD), 119 pages.*

*Primary Examiner* — Shahriar Zarrineh
(74) *Attorney, Agent, or Firm* — Carr & Ferrell LLP

(57) ABSTRACT

According to some exemplary embodiments, the present technology is directed to methods for managing a data incident, including receiving, via a risk assessment server, in response to an occurrence of the data incident, data incident data that comprises information corresponding to the data incident, the data incident further comprising intentional or unintentional compromise, disclosure or release of personal data or personally identifiable information to an untrusted or unauthorized environment, automatically generating, via the risk assessment server, a risk assessment and decision-support guidance whether the data incident is reportable from a comparison of the data incident data to privacy rules, the privacy rules comprising at least one European General Data Privacy Regulation (GDPR) rule, each rule defining requirements associated with data incident notification obligations, and providing, via the risk assessment server, the
(Continued)

risk assessment to a display device that selectively couples with the risk assessment server.

19 Claims, 17 Drawing Sheets

Related U.S. Application Data is a continuation-in-part of application No. 14/588,159, filed on Dec. 31, 2014, now Pat. No. 9,483,650, which is a continuation-in-part of application No. 14/311,253, filed on Jun. 21, 2014, now abandoned, which is a continuation of application No. 13/691,661, filed on Nov. 30, 2012, now Pat. No. 8,763,133, which is a continuation of application No. 13/396,558, filed on Feb. 14, 2012, now Pat. No. 8,707,445.

(51) Int. Cl.
  *G06F 21/57* (2013.01)
  *G06F 21/60* (2013.01)
  *G16H 10/60* (2018.01)

(52) U.S. Cl.
  CPC .......... *G16H 10/60* (2018.01); *H04L 63/0227* (2013.01); *H04L 63/1433* (2013.01); *H04L 63/0407* (2013.01)

(58) Field of Classification Search
  USPC .......................................................... 726/25
  See application file for complete search history.

(56) References Cited

U.S. PATENT DOCUMENTS

| | | | |
|---|---|---|---|
| 6,985,922 B1 | 1/2006 | Bashen et al. | |
| 7,287,008 B1* | 10/2007 | Mahoney | G06Q 40/00 705/35 |
| 7,343,303 B2* | 3/2008 | Meyer | G06Q 10/0635 705/325 |
| 7,676,426 B2* | 3/2010 | Lawrence | G06Q 20/10 705/38 |
| 7,739,132 B2 | 6/2010 | Denny, Jr. et al. | |
| 7,813,944 B1 | 10/2010 | Luk et al. | |
| 7,996,374 B1 | 8/2011 | Jones et al. | |
| 8,020,210 B2* | 9/2011 | Tippett | G06F 21/577 726/23 |
| 8,185,931 B1 | 5/2012 | Reeves | |
| 8,332,959 B2 | 12/2012 | Chen et al. | |
| 8,407,194 B1* | 3/2013 | Chaput | G06F 21/552 707/694 |
| 8,468,244 B2* | 6/2013 | Redlich | G06Q 10/06 705/50 |
| 8,650,067 B1* | 2/2014 | Moss | G06Q 30/0201 705/306 |
| 8,707,445 B2 | 4/2014 | Sher-Jan et al. | |
| 8,763,133 B2 | 6/2014 | Sher-Jan et al. | |
| 9,483,650 B2 | 11/2016 | Sher-Jan et al. | |
| 9,781,147 B2 | 10/2017 | Sher-Jan et al. | |
| 2002/0029157 A1 | 3/2002 | Marchosky | |
| 2002/0091549 A1 | 7/2002 | Provost et al. | |
| 2002/0120477 A1 | 8/2002 | Jinnett | |
| 2003/0056116 A1* | 3/2003 | Bunker, V | H04L 43/00 726/25 |
| 2003/0093365 A1 | 5/2003 | Halper et al. | |
| 2003/0135397 A1 | 7/2003 | Halow et al. | |
| 2003/0225690 A1 | 12/2003 | Eaton | |
| 2004/0098285 A1* | 5/2004 | Breslin | G06Q 10/10 713/193 |
| 2004/0128543 A1* | 7/2004 | Blake | H04L 63/0227 726/25 |
| 2004/0193870 A1* | 9/2004 | Redlich | G06F 21/6245 713/154 |
| 2004/0193907 A1 | 9/2004 | Patanella | |
| 2005/0044357 A1 | 2/2005 | Fano | |
| 2005/0066195 A1* | 3/2005 | Jones | G06F 21/577 726/4 |
| 2005/0132225 A1* | 6/2005 | Gearhart | G06Q 10/00 726/4 |
| 2005/0141941 A1 | 6/2005 | Narusawa et al. | |
| 2005/0171941 A1* | 8/2005 | Chen | G06F 17/30398 |
| 2005/0193430 A1* | 9/2005 | Cohen | G06F 21/577 726/25 |
| 2005/0273360 A1 | 12/2005 | Drucker et al. | |
| 2006/0020495 A1 | 1/2006 | Baker et al. | |
| 2006/0026042 A1* | 2/2006 | Awaraji | G06F 19/322 705/3 |
| 2006/0075503 A1* | 4/2006 | Bunker, V | G06F 11/324 726/25 |
| 2006/0101508 A1 | 5/2006 | Taylor | |
| 2006/0247947 A1 | 11/2006 | Suringa | |
| 2006/0277071 A1 | 12/2006 | Shufeldt | |
| 2006/0287953 A1* | 12/2006 | Chauhan | G06Q 40/00 705/39 |
| 2007/0038484 A1 | 2/2007 | Hoffner et al. | |
| 2007/0078668 A1 | 4/2007 | Pathria et al. | |
| 2007/0136814 A1 | 6/2007 | Lee et al. | |
| 2007/0250377 A1* | 10/2007 | Hill, Jr. | G06Q 10/00 705/7.13 |
| 2008/0059230 A1 | 3/2008 | Manning et al. | |
| 2008/0162496 A1 | 7/2008 | Postrel | |
| 2008/0177760 A1 | 7/2008 | Fein | |
| 2009/0024663 A1* | 1/2009 | McGovern | G06F 21/577 |
| 2009/0070434 A1 | 3/2009 | Himmelstein | |
| 2009/0210256 A1 | 8/2009 | Upadhyayula et al. | |
| 2009/0313049 A1 | 12/2009 | Joao et al. | |
| 2009/0319420 A1* | 12/2009 | Sanchez | G06Q 40/00 705/38 |
| 2010/0042440 A1 | 2/2010 | Joao | |
| 2010/0114607 A1 | 5/2010 | Kress et al. | |
| 2010/0199338 A1 | 8/2010 | Craddock et al. | |
| 2010/0205014 A1* | 8/2010 | Sholer | G06Q 40/08 705/4 |
| 2010/0262668 A1 | 10/2010 | Piett et al. | |
| 2010/0275263 A1* | 10/2010 | Bennett | G06F 21/577 726/25 |
| 2011/0126111 A1* | 5/2011 | Gill | G06F 21/55 715/736 |
| 2011/0289588 A1* | 11/2011 | Sahai | G06Q 90/00 726/25 |
| 2012/0072991 A1* | 3/2012 | Belani | H04W 4/001 726/25 |
| 2012/0143650 A1* | 6/2012 | Crowley | G06F 21/554 705/7.28 |
| 2012/0180133 A1* | 7/2012 | Al-Harbi | H04L 63/1433 726/25 |
| 2012/0331567 A1 | 12/2012 | Shelton | |
| 2013/0055337 A1* | 2/2013 | Choi | G06F 21/577 726/1 |
| 2013/0124223 A1 | 5/2013 | Gregg | |
| 2013/0212683 A1 | 8/2013 | Sher-Jan et al. | |
| 2013/0212692 A1 | 8/2013 | Sher-Jan et al. | |
| 2014/0259170 A1* | 9/2014 | Amsler | H04L 63/20 726/23 |
| 2014/0304822 A1 | 10/2014 | Sher-Jan et al. | |
| 2015/0113663 A1 | 4/2015 | Sher-Jan et al. | |
| 2016/0021133 A1 | 1/2016 | Sher-Jan et al. | |
| 2017/0270318 A1* | 9/2017 | Ritchie | G06Q 40/025 |
| 2017/0286717 A1* | 10/2017 | Khi | H04L 63/06 |
| 2018/0039794 A1 | 2/2018 | Sher-Jan | |
| 2018/0137305 A1* | 5/2018 | Barday | G06F 21/6245 |

\* cited by examiner

SYSTEMS AND METHODS FOR MANAGING DATA INCIDENTS

CROSS-REFERENCE TO RELATED APPLICATIONS

The present application is a continuation in part of U.S. Non-Provisional patent application Ser. No. 14/868,311 filed on Sep. 28, 2015 titled "Systems and Methods for Managing Data Incidents", which is a continuation in part of U.S. Non-Provisional patent application Ser. No. 14/588,159 filed on Dec. 31, 2014 titled "Systems and Methods for Managing Data Incidents", which is a continuation in part of U.S. Non-Provisional patent application Ser. No. 14/311,253 filed on Jun. 21, 2014 titled "Systems and Methods for Managing Data Incidents", which is a continuation of U.S. Non-Provisional patent application Ser. No. 13/691,661 filed on Nov. 30, 2012 and granted on Jun. 24, 2014 as U.S. Pat. No. 8,763,133 titled "Systems and Methods for Managing Data Incidents", which is a continuation of U.S. Non-Provisional patent application Ser. No. 13/396,558 filed on Feb. 14, 2012 and granted on Apr. 22, 2014 as U.S. Pat. No. 8,707,445 titled "Systems and Methods for Managing Data Incidents", which are all hereby incorporated by reference in entirety.

FIELD OF THE TECHNOLOGY

Embodiments of the disclosure relate to information privacy. More specifically, but not by way of limitation, the present technology relates to the management of data incidents.

BACKGROUND OF THE DISCLOSURE

Data incidents involve the exposure of sensitive information such as personally identifiable information and protected health information to third parties. Data incidents may comprise data breaches, privacy breaches, privacy or security incidents, and other similar events that result in the exposure of sensitive information to third parties.

SUMMARY OF THE DISCLOSURE

According to some exemplary embodiments, the present technology is directed to methods for managing a data incident, including receiving, via a risk assessment server, in response to an occurrence of the data incident, data incident data that comprises information corresponding to the data incident, the data incident further comprising intentional or unintentional compromise, disclosure or release of personal data or personally identifiable information to an untrusted or unauthorized environment, automatically generating, via the risk assessment server, a risk assessment and decision-support guidance whether the data incident is reportable from a comparison of the data incident data to privacy rules, the privacy rules comprising at least one European General Data Privacy Regulation (GDPR) rule, each rule defining requirements associated with data incident notification obligations, and providing, via the risk assessment server, the risk assessment to a display device that selectively couples with the risk assessment server. Further methods may include providing one or more data incident risk factor questions to the display device that elicit information corresponding to the data incident, receiving responses to the one or more data incident risk factor questions, providing the responses to the display device, and receiving confirmation of at least a portion of the responses. The at least one European General Data Privacy Regulation (GDPR) rule governs privacy breaches relative to at least one of personal data, special categories of personal data, or combinations thereof, and the risk assessment comprises a risk level that indicates the severity of the data incident relative to the at least one European General Data Privacy Regulation (GDPR) rule. Additionally, the risk level is associated with a color, wherein a hue of the color is associated with the severity of the data incident and a sensitivity of the data incident data as determined by the comparison.

According to various exemplary embodiments, the risk assessment defines one or more exceptions that apply to at least a portion of the data incident data based upon the comparison. The risk assessment may comprise at least a portion of the at least one European General Data Privacy Regulation (GDPR) rule and the method may include generating a notification schedule when the comparison indicates that the data incident violates and triggers a notification obligation according to the at least one European General Data Privacy Regulation (GDPR) rule. The method may also include providing an alert to the display device when the comparison indicates that the data incident violates and triggers a notification obligation according to the at least one European General Data Privacy Regulation (GDPR) rule. The notification schedule may include notification dates that are based upon a violated European General Data Privacy Regulation (GDPR) rule, along with notification requirements that describe information that is to be provided to a regulatory agency or to an affected individual whose personal data has been compromised, disclosed or released as a result of the data incident. The method may include receiving the information that is to be provided to a regulatory agency and storing the same in a content repository associated with the risk assessment server. The comparison may include modeling of the data incident data to the privacy rules to determine a severity and a data sensitivity of the data incident, and modeling the data incident data to determine severity and data sensitivity of the data incident by evaluating the data incident data relative to the at least one European General Data Privacy Regulation (GDPR) rule, and generating a risk assessment from the modeling.

Other exemplary embodiments may include a risk assessment server for managing a data incident, the server comprising a memory for storing executable instructions, a processor for executing the instructions, an input module stored in memory and executable by the processor to receive in response to an occurrence of the data incident, data incident data, the data incident data may include information corresponding to the data incident, the data incident further including the intentional or unintentional compromise, disclosure or release of personal data, personally identifiable information, or protected health information to an untrusted or unauthorized environment, a risk assessment generator stored in memory and executable by the processor to generate a risk assessment from a comparison of the data incident data to privacy rules, the privacy rules comprising at least one federal rule, at least one state rule, and at least one European General Data Privacy Regulation (GDPR) rule, each of the rules defining requirements associated with data incident notification laws, and a user interface module stored in memory and executable by the processor to provide the risk assessment to a display device that selectively couples with the risk assessment server. Additionally, the input module may generate one or more questions to the display device that elicit data incident data corresponding to the data incident, receive responses to the one or more questions, generate a summary of responses to the one or more questions, provide the summary to the display device, and receive confirmation of the summary. The risk assessment generator may generate a risk assessment that comprises a risk level that indicates the severity of the data incident relative to at least one of the at least one federal rule, the at least one state rule, or the at least one European General Data Privacy Regulation (GDPR) rule or combinations thereof.

According to further exemplary embodiments, the risk assessment generator creates a notification that one or more exceptions apply to at least a portion of the data incident data based upon modeling. The notification module may generate a notification schedule when modeling of the data incident indicates that the data incident violates and triggers a notification obligation according to any of the at least one federal rule, the at least one state rule, or the at least one European General Data Privacy Regulation (GDPR) rule, and the notification module may generate a notification schedule that includes notification dates that are based upon a violated rule, along with notification requirements that describe information that is to be provided to a regulatory agency. Additionally, a reporting module stored in memory and executable by the processor may receive the information that is to be provided to the regulatory agency and an affected individual and store the same in a content repository associated with the risk assessment server.

According to many exemplary embodiments, the privacy rules further include at least one Network and Information Security Directive (NISD) rule of a European Member State. The privacy rules may also include at least one rule under Canada's Personal Information Protection and Electronic Documents Act (PIPEDA).

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 16 illustrates an exemplary GUI in the form of a Network and Information Security Directive (NISD) rule risk assessment page of a European Member State; and FIG. 17 illustrates an exemplary GUI in the form of a Canadian Personal Information Protection and Electronic Documents Act (PIPEDA) rule risk assessment page.

DETAILED DESCRIPTION

Figure 1:
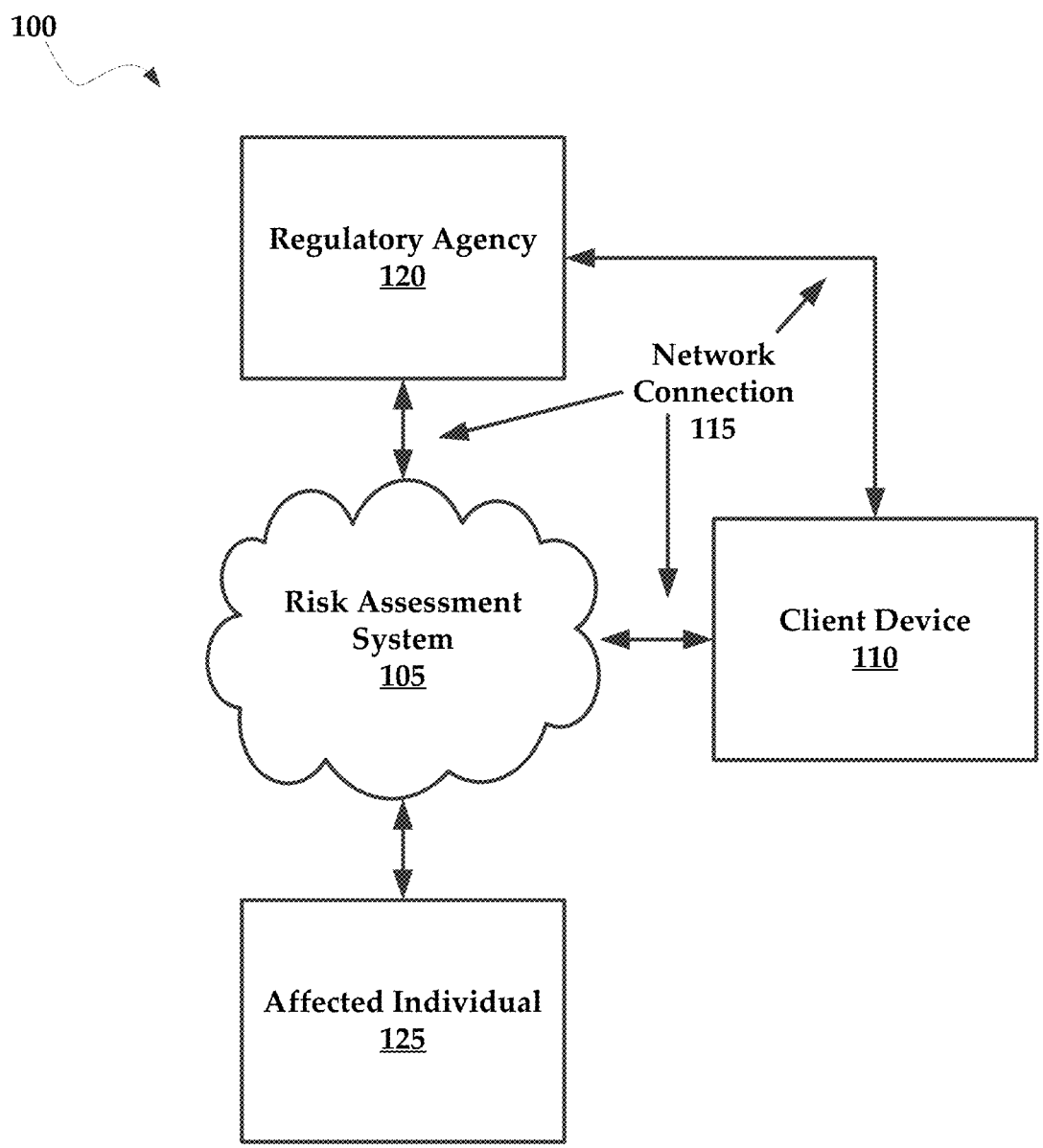
FIG. 1 illustrates an exemplary system for practicing aspects of the present technology.

In the following description, for purposes of explanation, numerous specific details are set forth in order to provide a thorough understanding of the disclosure. It will be apparent, however, to one skilled in the art, that the disclosure may be practiced without these specific details. In other instances, structures and devices are shown at block diagram form only in order to avoid obscuring the disclosure.

Generally speaking, the present technology may be directed to managing data incidents. It will be understood that the terms "data incident" may be understood to encompass privacy incidents, security incidents, privacy breaches, data breaches, data leaks, information breaches, data spills, or other similarly related events related to the intentional or unintentional release of protected information to an unauthorized or untrusted environment. This protected information may be referred to as personally identifiable information (hereinafter "PII/PHI") or protected health information (e.g., an entity that has been entrusted with the PHI such as a hospital, clinic, health plan, and so forth).

PII/PHI may encompass a wide variety of information types, but non-limiting examples of PII comprise an individual's full name, a date of birth, a birthplace, genetic information, biometric information (face, finger, handwriting, etc.), national identification number (e.g., social security), vehicle registration information, driver's license numbers, credit card numbers, digital identities, and Internet Protocol addresses.

Other types of information may, in some instances, be categorized as PII/PHI, such as an individual's first or last name (separately), age, residence information (city, state, county, etc.), gender, ethnicity, employment (salary, employer, job description, etc.), and criminal records—just to name a few. It is noteworthy to mention that the types of information that are regarded as PII are subject to change and therefore may include more or fewer types of information that those listed above. Additionally, what constitutes PII/PHI may be specifically defined by a local, state, federal, or international data privacy laws.

While entities that are subject to these privacy laws may be referred to in a variety of ways, for consistency and clarity an entity (either individual or corporate) that is entrusted with PII/PHI will hereinafter be referred to as an "entrusted entity."

It will be understood that the privacy laws contemplated herein may comprise details regarding not only how an entrusted entity determines if a data incident violates the law, but also when the provision of notification to one or more privacy agencies and/or the customers of the entrusted entity is warranted.

According to some embodiments, the present technology is directed to generating risk assessments for data incidents. These risk assessments provide specific information to the entrusted entity regarding the severity of the data incident relative to a state or federal rule. Additionally, the risk assessment provides information regarding the data sensitivity for the data incident. That is, the risk assessment may determine if the type of data that was exposed is highly sensitive information. As mentioned before, some PII/PHI may be considered more sensitive than others. For example, a social security number may be more sensitive than a gender description, although the relative sensitivity for different categories of PII/PHI are typically delineated in the privacy rules and may require delineation in the context of each data incident.

The present technology may determine the severity and/or data sensitivity for a data incident by collecting data incident data from an entrusted entity. This data incident data may be compared against one or more selected privacy rules to determine the severity and/or data sensitivity for the data incident. In some instances, the present technology may model the data incident data to the one or more privacy rules.

According to some embodiments, the privacy rules described herein may comprise the content of a state and/or federal statute. In other embodiments, the privacy rules may comprise abstracted or mathematically expressed rules that have been generated from the text of the state and/or federal statute. Applying a privacy rule to the data incident data may yield values for the severity and/or the data sensitivity of the data incident.

In some embodiments, the risk assessment may provide indication to the entrusted entity that an obligation has occurred. More specifically, if the severity of the data incident and/or the data sensitivity of the data incident when compared to the privacy rules indicates that the data incident has violated at least one of the privacy rules, the risk assessment may include an indication that an obligation has been created. An obligation may require the entrusted entity to notify subjected individuals that their PII/PHI has been potentially exposed. The obligation may also require that notification be provided to a regulating authority such as the department of Health and Human Services (HHS), Office for Civil Rights (OCR), Federal Trade Commission, a state agency, or any agency that regulates data incident notification.

The present technology allows entrusted entities to model data incident data to privacy rules which include at least one state rule and at least one federal rule. In some instances, entrusted entities may model data incidents to the rules of several states to generate risk assessments of each of the states. This is particularly helpful when entrusted entities service customers in many states. Moreover, each of these states may have differing notification requirements, along with different metrics for determining when a data incident requires notification.

In some embodiments, the risk assessment may include a risk level that is associated with a color. More specifically, a hue of the color is associated with the severity of the data incident as determined by the comparison or modeling if the data incident data.

According to the present disclosure, the present technology may generate a notification schedule for an entrusted entity along with mechanisms that aid the entrusted entity in gathering pertinent information that is to be provided to the customer and/or one or more regulator agencies.

These and other advantages of the present technology will be described in greater detail with reference to the collective FIGS. 1-15.

FIG. 1 illustrates an exemplary system 100 for practicing aspects of the present technology. The system 100 may include a risk assessment system, hereinafter "system 105" that may be implemented in a cloud-based computing environment, or as a web server that is particularly purposed to manage data incidents.

In general, a cloud-based computing environment is a resource that typically combines the computational power of a large grouping of processors and/or that combines the storage capacity of a large grouping of computer memories or storage devices. For example, systems that provide a cloud resource may be utilized exclusively by their owners; or such systems may be accessible to outside users who deploy applications within the computing infrastructure to obtain the benefit of large computational or storage resources.

The cloud may be formed, for example, by a network of web servers, with each web server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depend on the type of business associated with the user.

In other embodiments, the system 105 may include a distributed group of computing devices such as web servers that do not share computing resources or workload. Additionally, the system 105 may include a single computing device, such as a web server, that has been provisioned with one or more programs that are utilized to manage data incidents.

End users may access and interact with the system 105 via the client device 110 through a web-based interface, as will be discussed in greater detail infra. Alternatively, end users may access and interact with the system 105 via a downloadable program that executes on the client device 110. The system 105 may selectively and communicatively couple with a client device 110 via a network connection 115. The network connection 115 may include any one of a number of private and public communications mediums such as the Internet.

Additionally, the system 105 may collect and transmit pertinent information to regulatory agencies, such as regulatory agency 120, as will be discussed in greater detail infra. In some instances, notification may also be provided to affected individuals 125.

The system 105 may be generally described as a mechanism for managing data incidents. The system 105 may manage a data incident by collecting data incident data for the data incident and then modeling the data incident data to privacy rules. As mentioned previously, the privacy rules may include at least one state rule and at least one federal rule. The modeling of the data incident data may be utilized to generate a risk assessment for the data incident. The risk assessment may be utilized by an entrusted entity to determine how best to respond to the data incident. The system 105 is provided with a risk assessment application 200 that will be described in greater detail with reference to FIG. 2.

Figure 2:
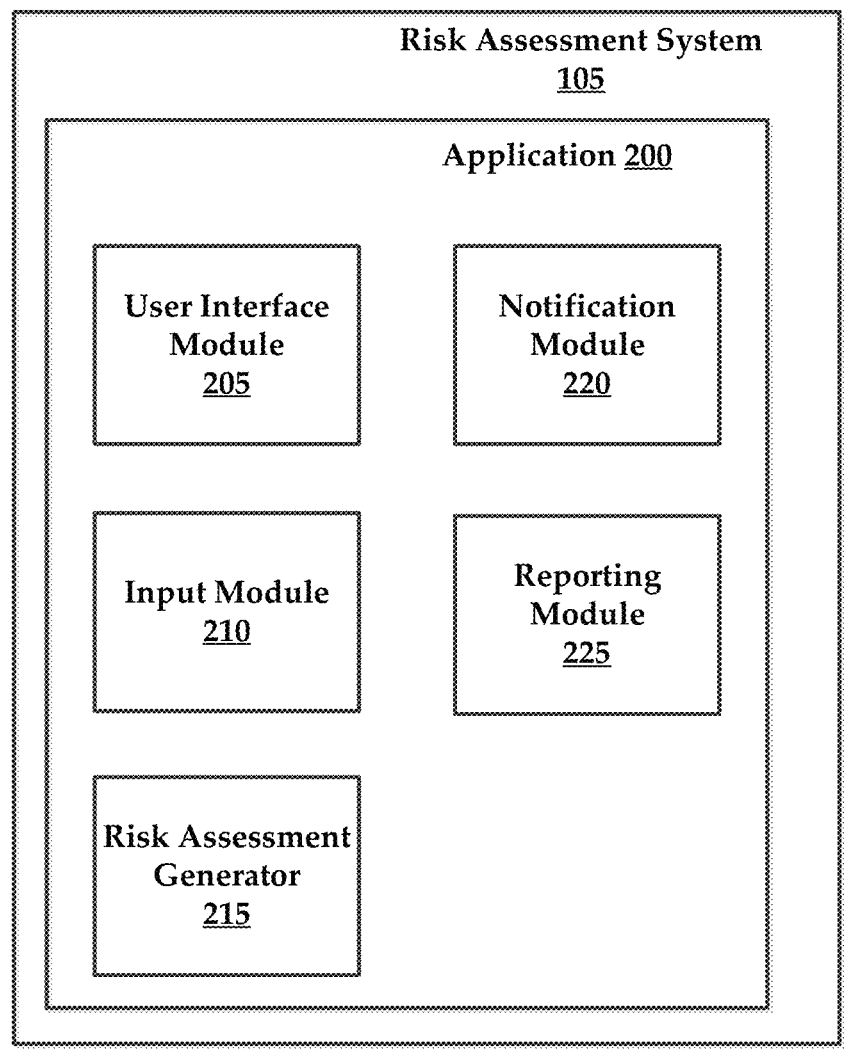
FIG. 2 illustrates an exemplary conversion application for managing data incidents.

FIG. 2 illustrates a risk assessment application, hereinafter referred to as application 200. In accordance with the present disclosure, the application 200 may generally include a user interface module 205, an input module 210, a risk assessment generator 215, a notification module 220, and a reporting module 225. It is noteworthy that the application 200 may include additional modules, engines, or components, and still fall within the scope of the present technology. Moreover, the functionalities of two or more modules, engines, generators, or other components may be combined into a single component.

As used herein, the terms "module," "generator," and "engine" may also refer to any of an application-specific integrated circuit ("ASIC"), an electronic circuit, a processor (shared, dedicated, or group) that executes one or more software or firmware programs, a combinational logic circuit, and/or other suitable components that provide the described functionality. In other embodiments, individual modules of the application 200 may include separately configured web servers. Also, the application 200 may be provisioned with a cloud.

Generally described, the application 200 allows entrusted entities to input data incident data, have one or more risk assessments generated, and receive the one or more risk assessments, along with notifications schedules, as required.

An entrusted entity may interact with the application 200 via a graphical user interface that is provisioned as a web-based interface. The web-based interface may be generated by the user interface module 205. It will be understood that the user interface module 205 may generate a plurality of different graphical user interfaces that allow individuals associated with the entrusted entity (e.g., privacy officer, compliance officer, security officer, attorney, employee, agent, etc.) to utilize interact with the application 200. Examples of graphical user interfaces that are generated by the user interface module 205 are provided in FIGS. 3-13, which will be described in greater detail infra.

Upon the occurrence of a data incident, the input module 210 may be executed to receive data incident data from the entrusted entity. It is noteworthy that the user interface module 205 may generate different types of graphical user interfaces that are tailored to obtain specific types of data incident data from the entrusted entity.

Initially, it may be desirous for the entrusted entity to establish a profile that may be utilized to determine if the entity that is using the application 200 is, in fact, an entrusted entity. It is noteworthy that to mention that the determination of what entities are entrusted entities depends upon the privacy rule. For example, an entity may be considered to be an entrusted entity under a particular federal statute, but may not be labeled an entrusted entity under one or more state statutes. Likewise, different states may have discrepant methods for determining who constitutes an entrusted entity.

Therefore, it may be advantageous to determine information about the entity such as what types of information they collect and where they conduct business. The input module 210 may be executed to solicit pertinent information from the entity that may be utilized to determine if the entity is an entrusted entity. Again, the entity may specify a plurality of states in which they conduct business, or the states of residence/domicile for customers with which they conduct business.

If it is determined that the entity is an entrusted entity, the input module may further solicit data incident data for one or more data incidents. Pertinent data incident data may include the type of data that was compromised, the date of compromise, the amount of data that was compromised, were there security measures in place (e.g., encryption, redaction, etc.), was the incident intentional or unintentional, was the incident malicious or non-malicious, how the data was compromised (e.g., theft of laptop, database security failure, lost storage media, hacked application, hacked computing device (e.g., web server, email server, content repository, etc.), and other types of information that assist in determining a risk level for the data incident as well as any notification obligations.

In some instances, rather than soliciting generalized data incident data from the entrusted entity, the input module 210 may select questions that solicit data that is particularly relevant to the privacy rules to which the entrusted entity is subject. For example, if a privacy rule specifies that a threshold amount of records must be exposed in order to create an obligation, the end user may be asked if their amount of exposed records meets or exceeds that threshold amount. This type of tailored questioning narrows the analysis that is performed of the data incident data and improves the efficiency of the risk assessment process.

Once the data privacy data has been received, the input module 210 may generate a summary of the data privacy data (or at least a portion of the data) that is provided to the entrusted entity via a graphical user interface generated by the user interface module 205.

The input module 210 may be configured to solicit confirmation from the entrusted entity that the data privacy data in the summary is correct. If the data is incorrect, the entrusted entity may go back and correct the errant data.

As mentioned briefly above, the input module 210 may solicit and receive one or more selections of one or more states from the entrusted entity. Using the selections, the input module 210 may select one or more state statutes based upon the one or more selections. Also, the input module 210 may generate at least one state rule for each selected state statute. Additionally, one or more federal rules may be selected and generated as well.

The input module 210 may generate a state or federal privacy rule by evaluating the state/federal statute and creating a plurality of qualifications from the statutes. Qualifications for a statute may include, for example, thresholds or formulas that are used to determine if the data incident data of a data incident violates the statute. Stated otherwise, these qualifications may be used as a mathematical model of a statute. Data incident data may be evaluated in light of the model. The resultant modeling may be used to generate a risk assessment for the data incident.

The risk assessment generator 215 may be executed to generate one or more risk assessments for the data incident. The risk assessment generator 215 may model the data incident data to the selected or determined privacy rules to determine if an obligation has been triggered under a privacy rule.

Again, risk assessments may be generated by modeling the data incident data to at least one state rule and at least one federal rule. The risk assessment may combine risk levels for each rule into a single risk assessment, or individual risk assessments may be generated for each rule.

Modeling of the data incident data to a privacy rule (either state or federal) by the risk assessment generator 215 may result in the generation of a severity value and a data sensitivity value for the data incident. The severity value may represent the extent to which PII/PHI has been compromised, while the data sensitivity value may represent the relative sensitivity of the PII/PHI that was compromised. These two factors may independently or dependently serve as the basis for determining if a notification obligation exists. For example, if the severity value meets or exceeds a threshold amount, a notification obligation may exist. If the data sensitivity value meets or exceeds a threshold amount, a notification obligation may exist. In some instance, a notification obligation may only exist if the sensitivity value and the data sensitivity value both exceed threshold amounts. Again, the threshold amounts are specified by the particular privacy rule that is being applied to the data incident data.

The risk assessment generator 215 may also determine and apply exceptions that exist in a state or federal statute during the generation of a risk assessment. These exceptions may be noted and included in the risk assessment.

Figure 7:
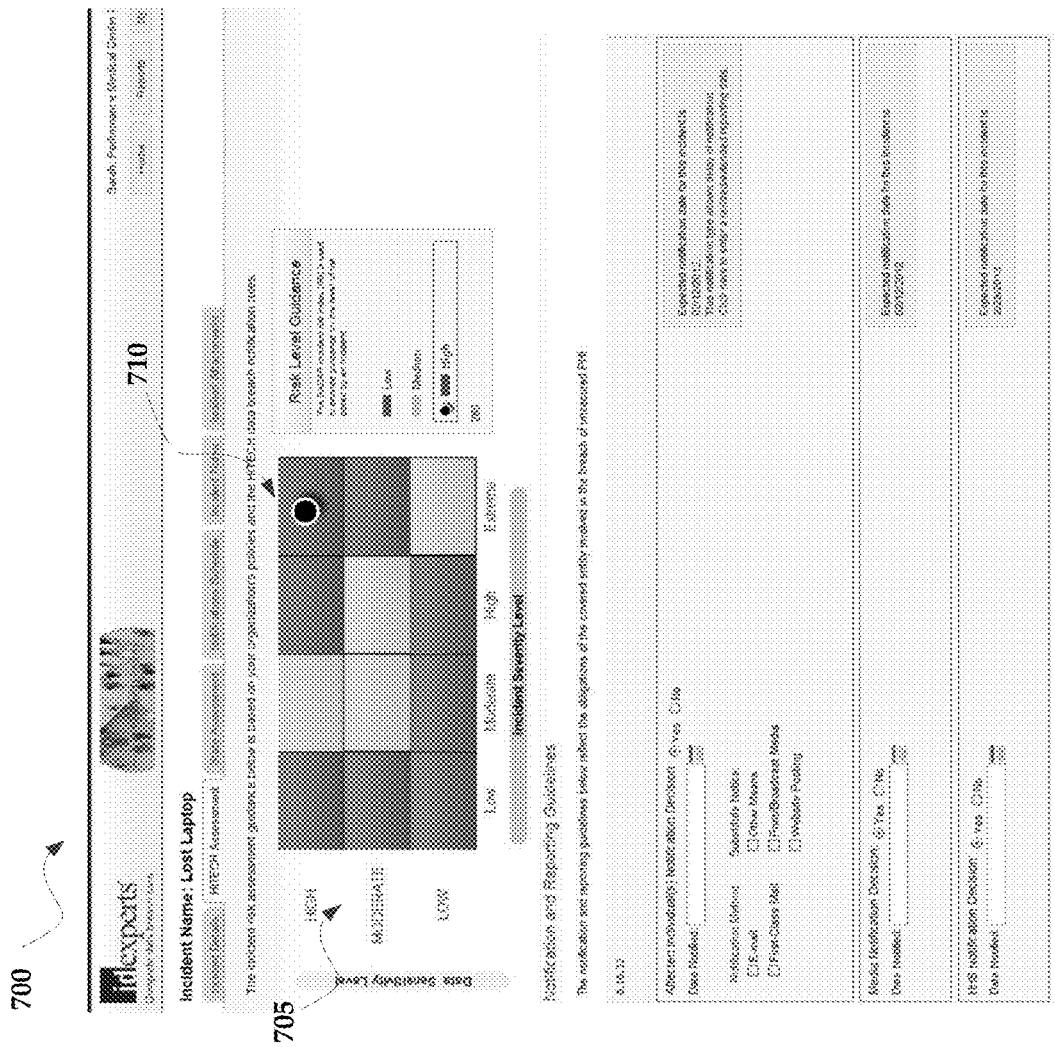
FIG. 7 illustrates an exemplary GUI in the form of a federal risk assessment page.

The risk assessment generator 215 may create a visual indicator such as a risk level or heat map that assists the entrusted entity in determining if a data incident is relatively severe or is relatively benign. This visual indicator may be included in the risk assessment. For example, a risk assessment may include a risk level that includes a visual indicator such as a colored object. In some embodiments, a hue of the object is associated with the severity of the data incident where red may indicate a severe risk and green may indicate a benign risk, with orange or yellow hues falling somewhere therebetween. Examples of heat maps and risk levels indicators are illustrated in FIG. 7.

Included in the risk assessment, in some instances, is a summary of sections of the state or federal privacy statute. For example, with regard to a state specific assessment, the risk assessment generator 215 may generate an outline of key information about the state statute that was utilized to generate the state specific risk assessment. This outline may be displayed to the entrusted entity via a user interface.

If the risk assessment generator 215 determines that the data incident violates one or more statutes (e.g., high severity value, PII/PHI is very sensitive, etc.), the notification module 220 may be executed to generate a notification schedule. The notification schedule may be generated based upon a data associated with the data incident. That is, the statute may specify when notification is to occur, relative to the date that PII was exposed.

Additionally, the notification schedule informs the entrusted entity as to what types of information are to be provided, along with the regulatory bodies to which the information should be provided. Again, the notification schedule may be generated from the statute itself. For example, a statute may specify that the data incident data (or a portion of the data incident data) collected by the input module 210 should be provided to a particular state agency within a predetermined period of time. Again, if a plurality of states have been designated or selected, the notification schedule may include notification dates for each state agency.

To assist the entrusted entity in meeting their notification obligations, the reporting module 225 may be executed to gather pertinent documents or other information from the entrusted entity and transmit these documents to the required reporting authorities. The reporting module 225 may prompt the entrusted entity to attach documents via a user interface. Once attached, these documents/data may be stored in a secured repository for submission to regulatory agency. In other instances, the entrusted entity may transmit required information directly to the regulatory agency.

Additionally, the reporting module 225 may provide required notifications to affected individuals, such as the individuals associated with the PII/PHI that was compromised.

FIGS. 3-13 illustrate various exemplary graphical user interfaces (GUI) that are generated by the user interface module 205. Each of the exemplary user interfaces will be described below.

Figure 3:
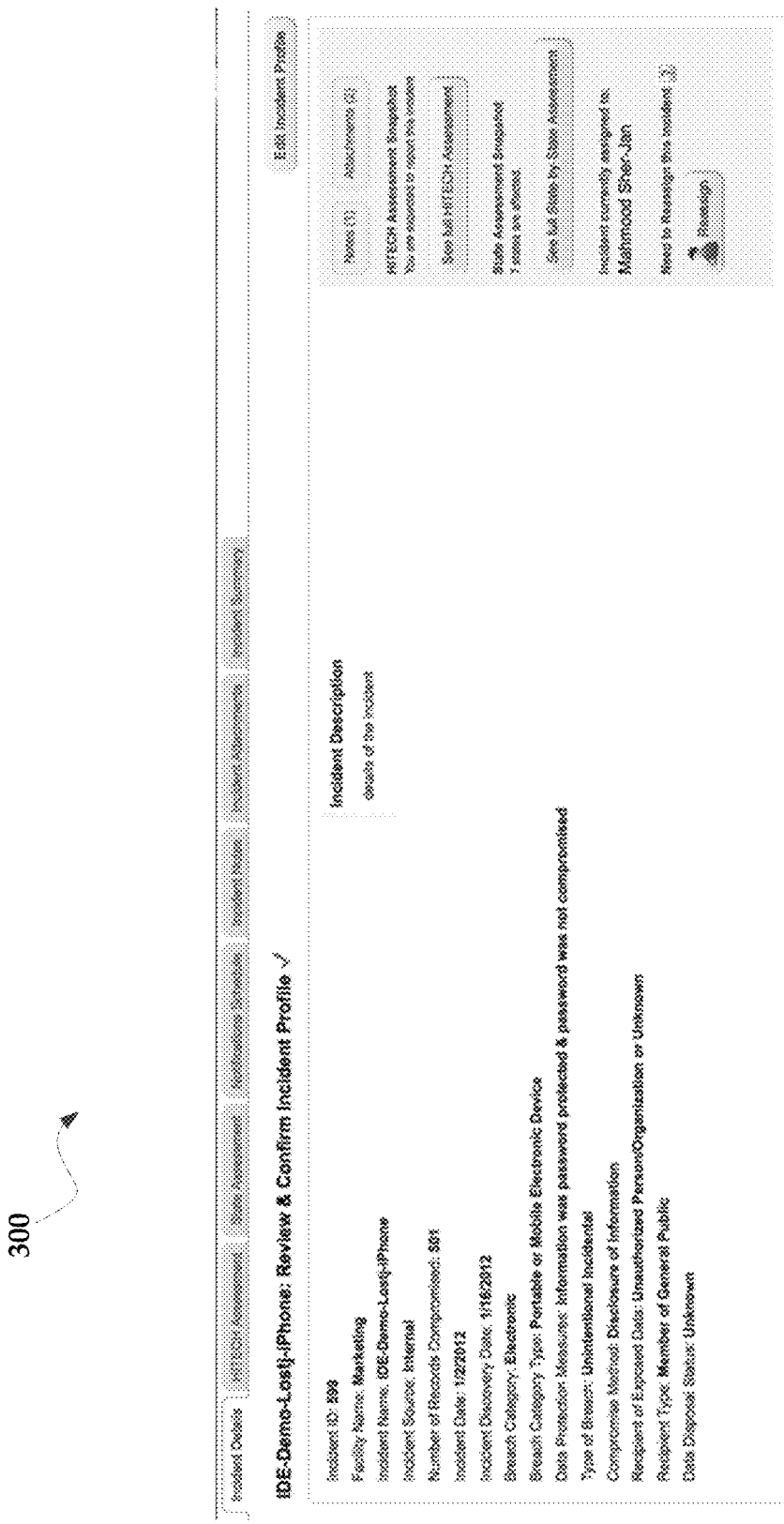
FIG. 3 illustrates an exemplary GUI in the form of a data incident details page.

FIG. 3 illustrates an exemplary GUI in the form of a data incident summary page. The summary page 300 includes a plurality of received answers to questions that were provided to the entrusted entity. Responses that were received indicate that the data incident involved the loss of a cellular telephone, an incident date of Jan. 2, 2012, an incident discover date of Jan. 16, 2012, and other pertinent data incident data.

Figure 4:
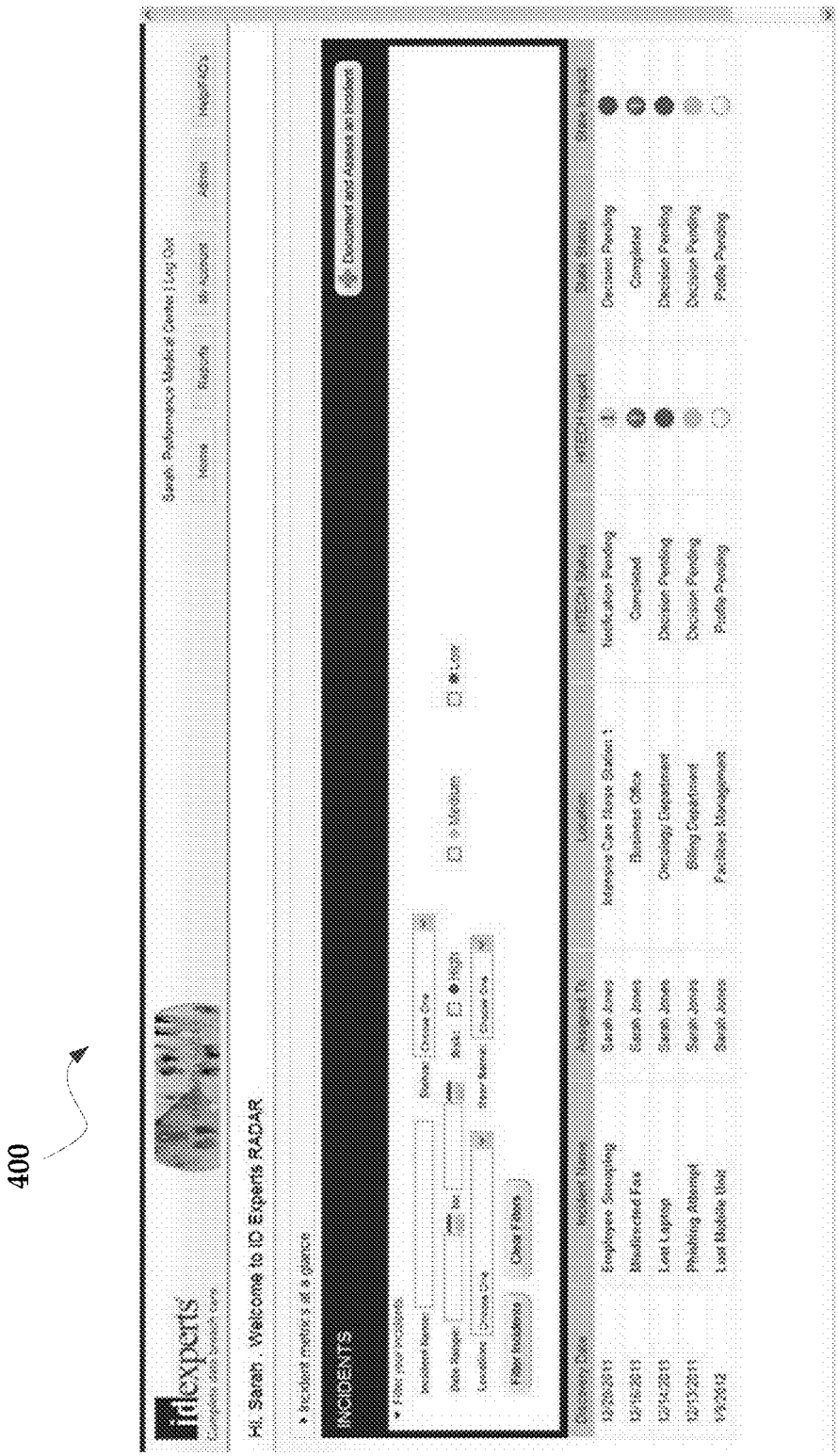
FIG. 4 illustrates an exemplary GUI in the form of a data incident dashboard.

FIG. 4 illustrates an exemplary GUI in the form of a data incident dashboard page 400. The page 400 includes listing of pending and completed risk assessments for a plurality of data incidents. Each entry may include a risk indicator having a particular color to help the entrusted entity in quickly determining data incidents that are high risk. A risk indicator may be associated with a particular privacy rule. For example, a risk indicator for an Employee Snooping data incident indicates that a moderately high risk is associated with the data incident relative to HITECH rules (e.g., rules associated with the compromise of PHI). This moderately high risk is indicated by a yellow dot placed within a row of a "HITECH Status" column. Additionally, a severe risk is associated with a state privacy rule. This severe risk is indicated by a red dot placed within a row of a "State Impact" column.

Figure 5:
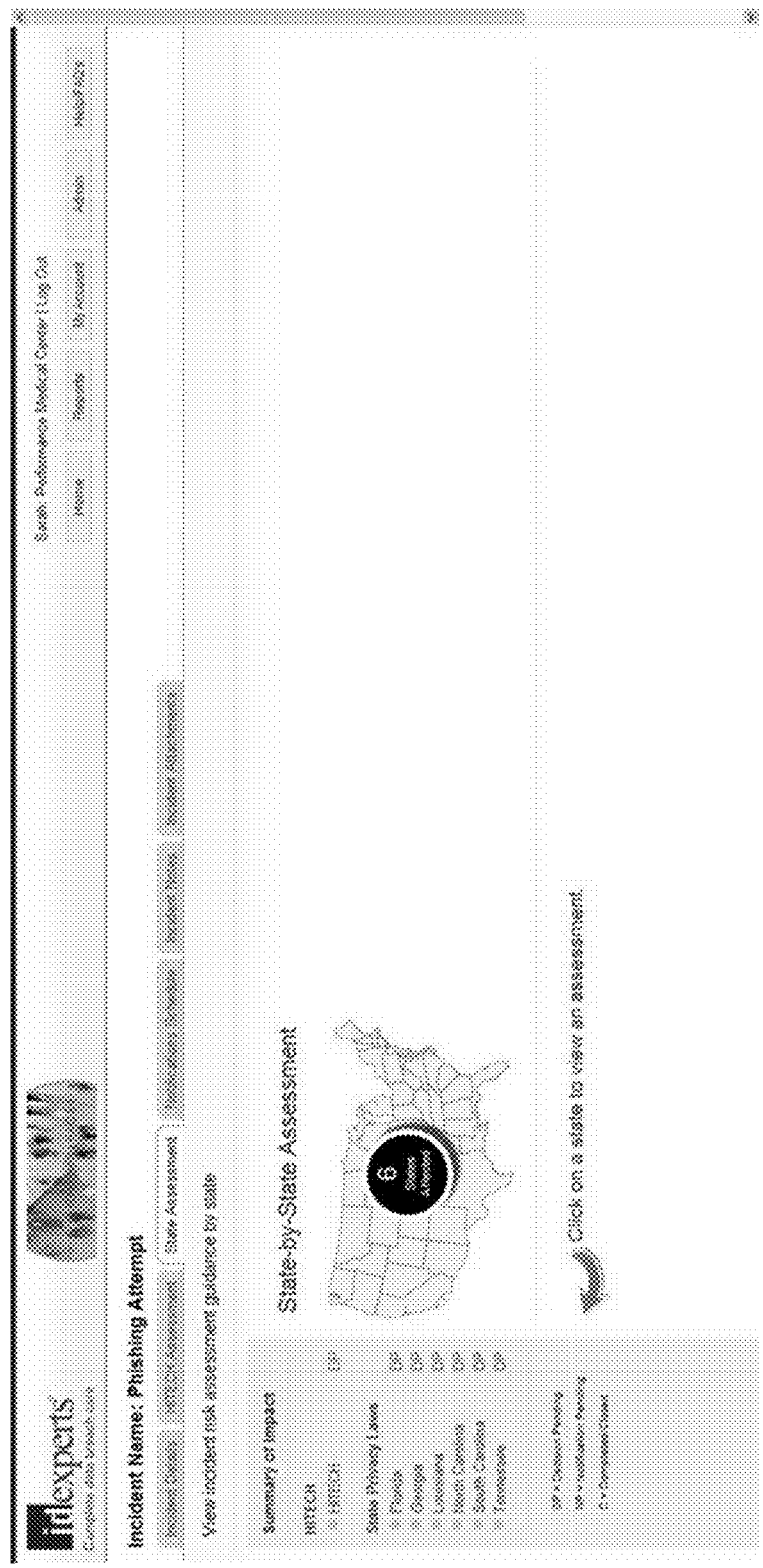
FIG. 5 illustrates an exemplary GUI in the form of a state specific risk assessment selection and notification page.

FIG. 5 illustrates an exemplary GUI in the form of a state specific selection and notification page 500. The notification page is shown as comprising an image that informs the trusted entity that six states have been affected by the data incident. To view a risk assessment for each state, the trusted entity may click on any of the stated listed in the leftmost frame.

Figure 6:
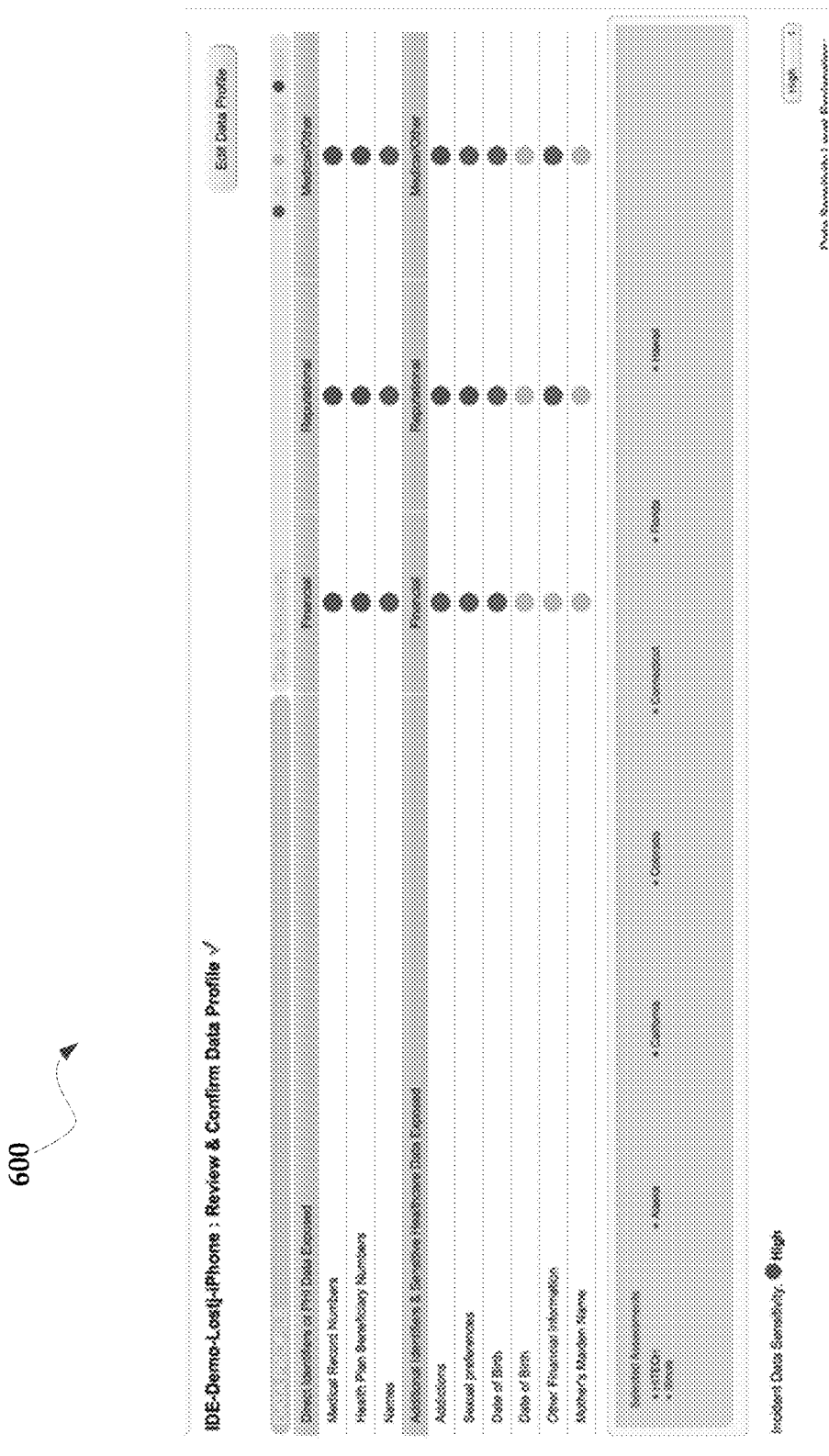
FIG. 6 illustrates an exemplary GUI in the form of a data sensitivity level evaluation and selected federal and state specific risk assessments page.

FIG. 6 illustrates an exemplary GUI in the form of a data sensitivity level evaluation page 600. The page includes a plurality of data sensitivity indicators the sensitivity for different types of PII/PHI that were compromised by the data incident. For example, medical record numbers are shown in red as being highly sensitive. Moreover, medical record numbers may pose financial, reputational, and medical harm, which are just some of the dimensions of potential harm caused by compromise of PII/PHI. In contrast, the data incident also compromised individual's date of birth. As determined by entrusted entity, that type of PII/PHI is not considered highly sensitive and thus, has been depicted in green.

FIG. 7 illustrates an exemplary GUI in the form of a risk assessment page 700. The risk assessment page 700 includes a heat map 705 and corresponding risk level indicator 715, which is placed within the heat map 705. The heat map 710 includes a grid where vertical placement indicates data sensitivity level and horizontal placement indicates severity level. As is shown, as the sensitivity and severity levels increase, so do the odds that the data incident may trigger an obligation to notify affected parties. In this instance, the risk level is high because the sensitivity level is high and the severity level is extreme.

Positioned below the heat map 705 is a notification schedule that includes not only the obligations for the entrusted entity, but also the expected notification dates. Again, this schedule may be based upon requirements included in the violated statute.

Figure 8:
FIG. 8 illustrates an exemplary GUI in the form of a state specific risk assessment page.

FIG. 8 illustrates an exemplary GUI in the form of a state specific risk assessment page 800. The page 800 includes a risk assessment for the State of California. The state impact is shown as high and a summary of the types of PII/PHI that were exposed are summarized below the state impact indicator. Similarly to the risk assessment page 700 of FIG. 7, a notification schedule is included on the state specific risk assessment page 800. It is noteworthy that a state specific risk assessment page may be generated for each affected state (such as the affected states listed on the state specific selection and notification page 500 of FIG. 5.

Figure 9:
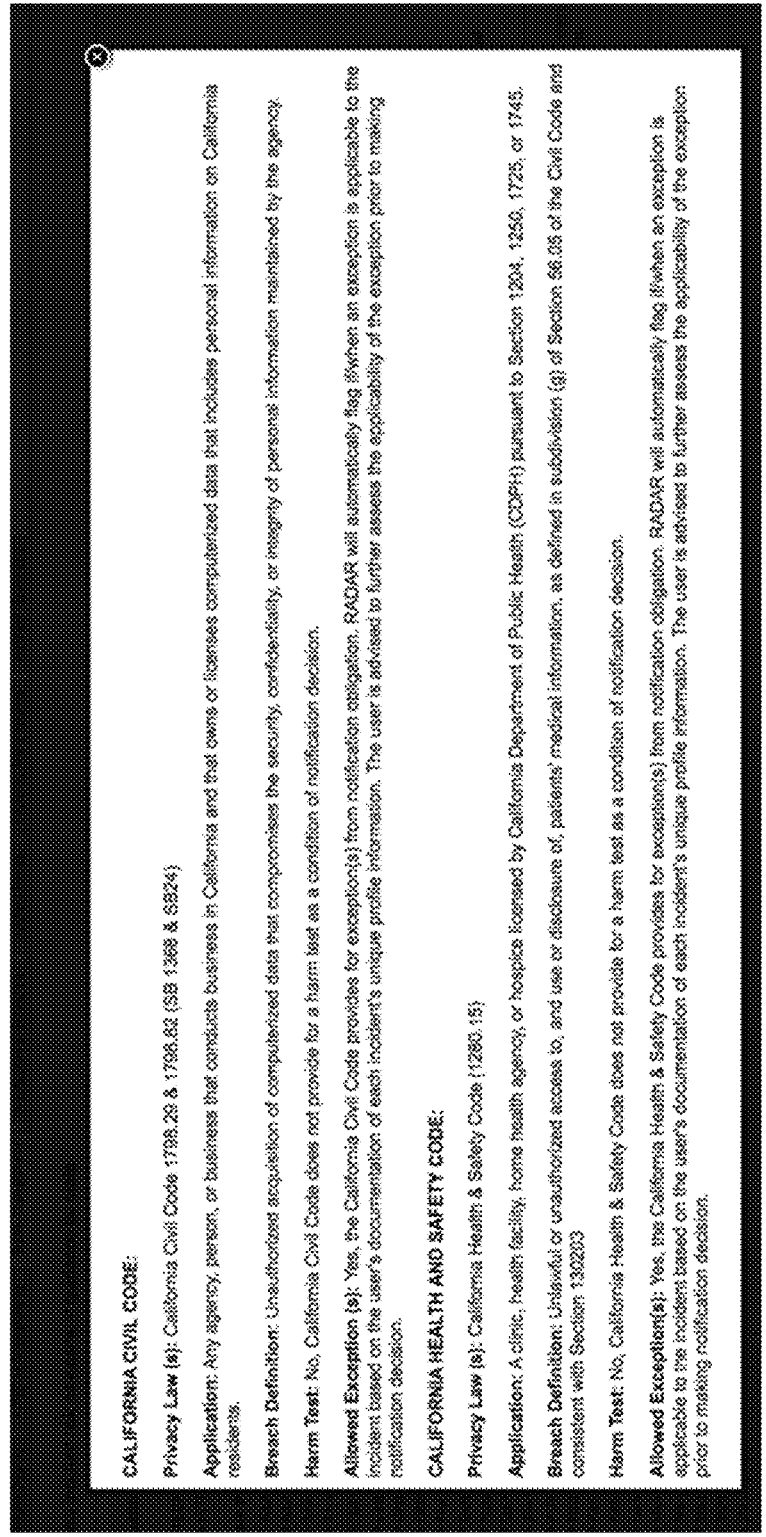
FIG. 9 illustrates an exemplary GUI in the form of a statute summary page.

FIG. 9 illustrates an exemplary GUI in the form of a statute summary page 900. The statute summary page 900 includes a copy (or a portion) of the privacy statutes (California Civil Code 1798.29 & 1798.82; California Health and Safety Code 1280.15) that were utilized to generate the state specific risk assessment that was provided on in FIG. 8. Note that the summary also includes whether the state statutes include harm test and exceptions which are flagged by the risk assessment generator 215 according to the specific privacy statutes.

Figure 10:
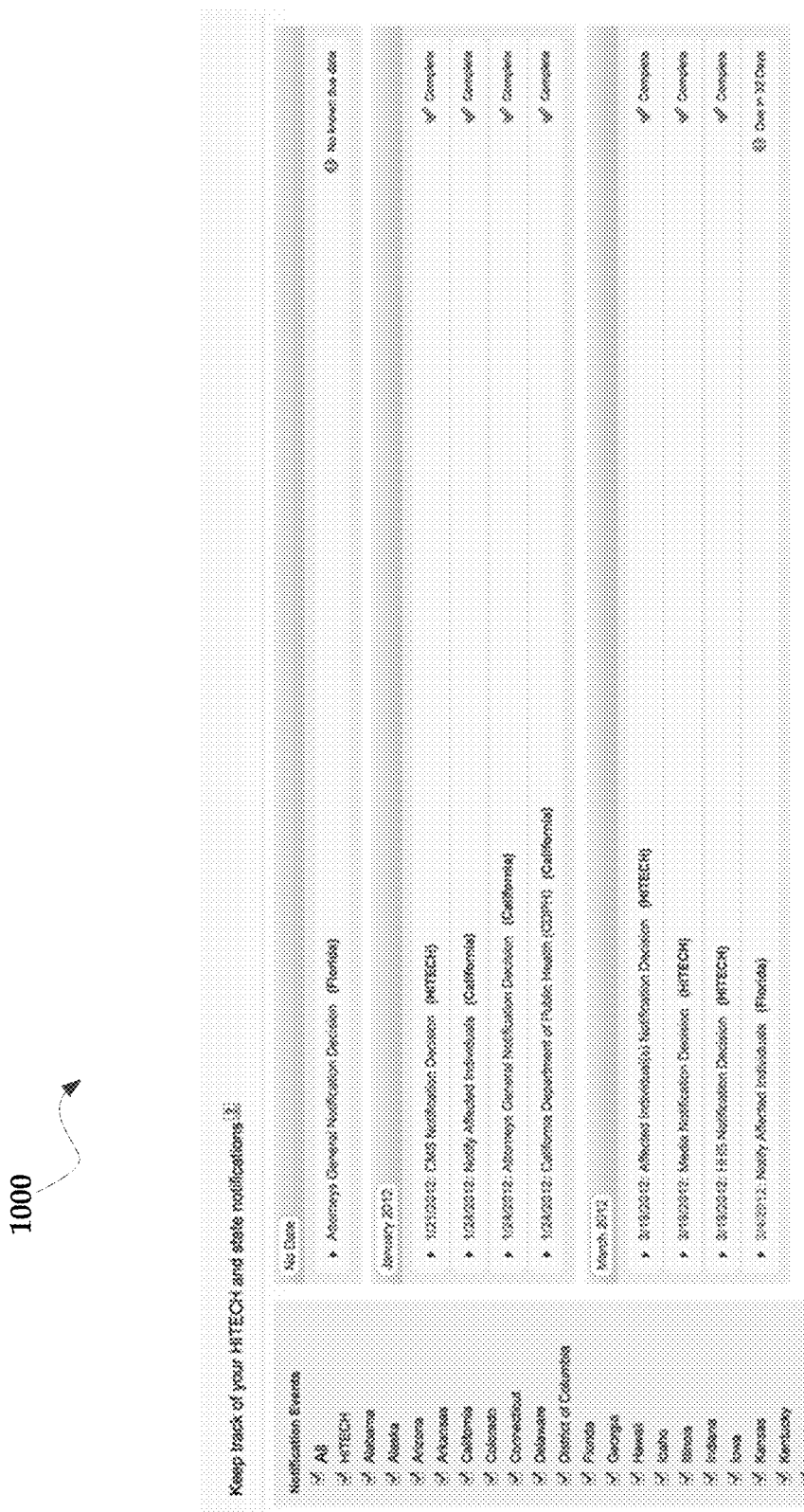
FIG. 10 illustrates an exemplary GUI in the form of an aggregated notification schedules page.

FIG. 10 illustrates an exemplary GUI in the form of an aggregated notification page 1000. The page 1000 includes a notification schedule for each affected privacy statues (e.g., federal and state(s)) relative to one or more data incidents. A list of notification events is provided and the end user may utilize the check boxes to select which states (or federal) risk assessment notification schedules are displayed.

Figure 11:
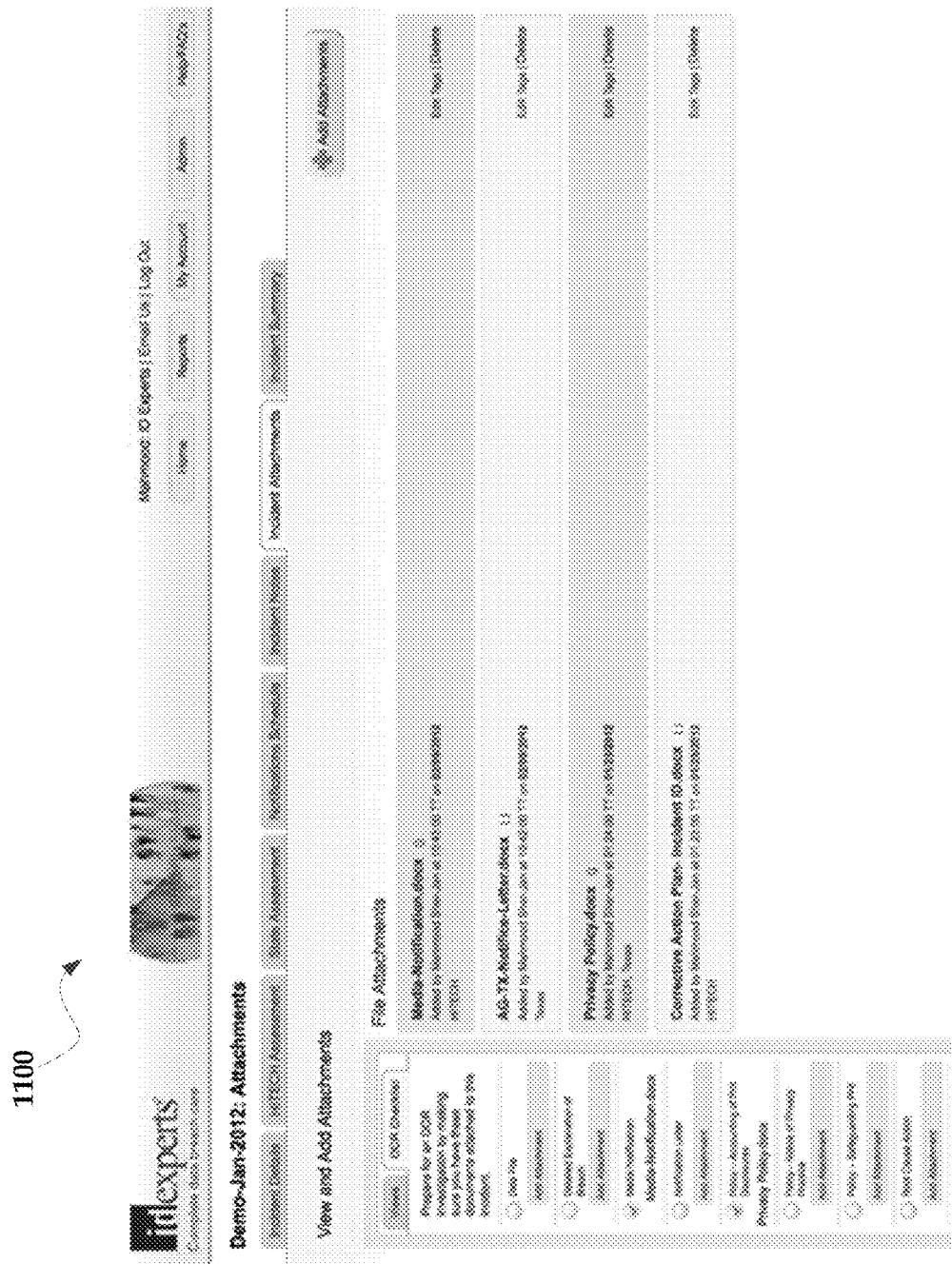
FIGS. 11-13 illustrate exemplary GUIS that are utilized to collect, store, and transmit pertinent documents or data.
Figure 12:
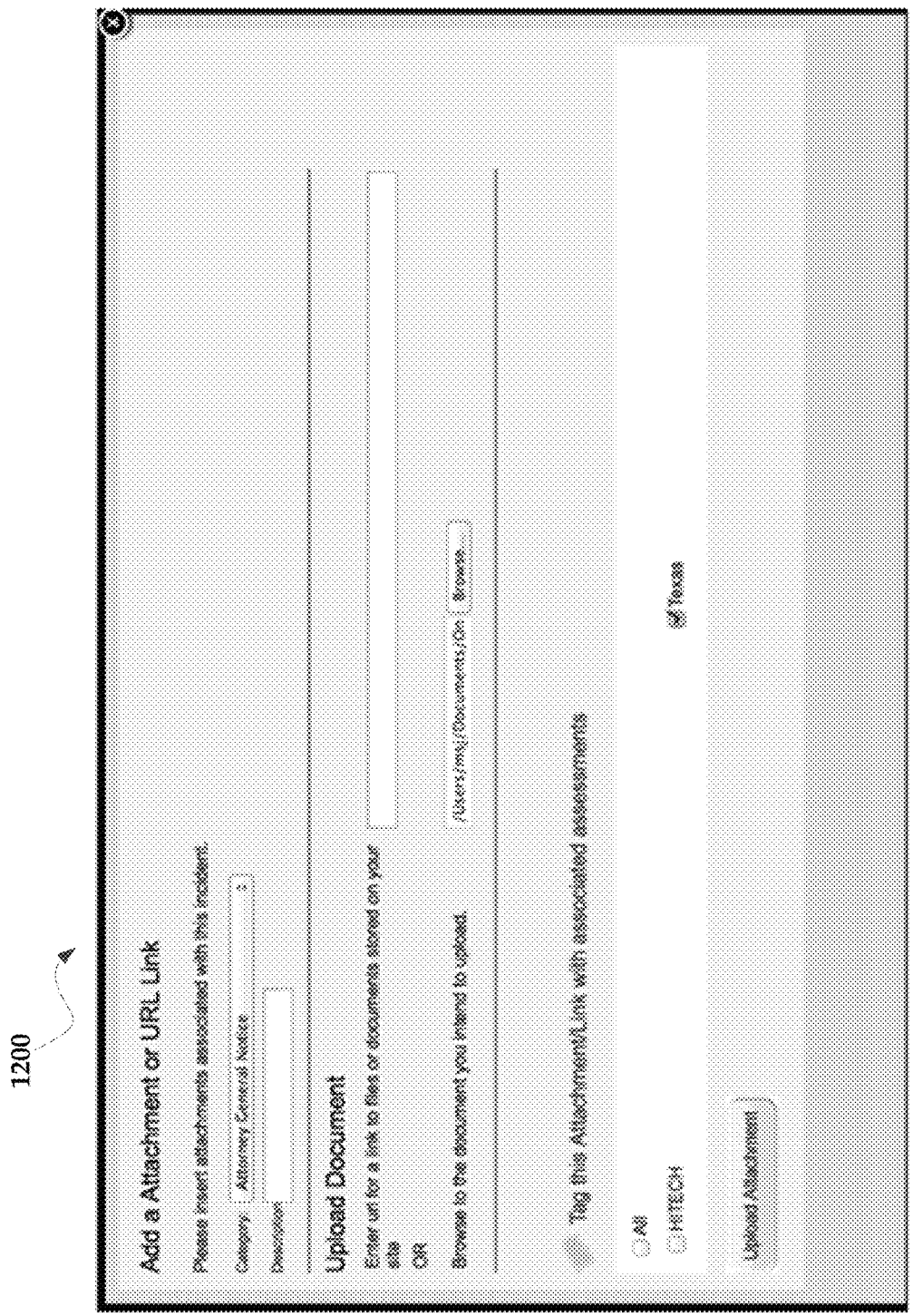
Figure 13:
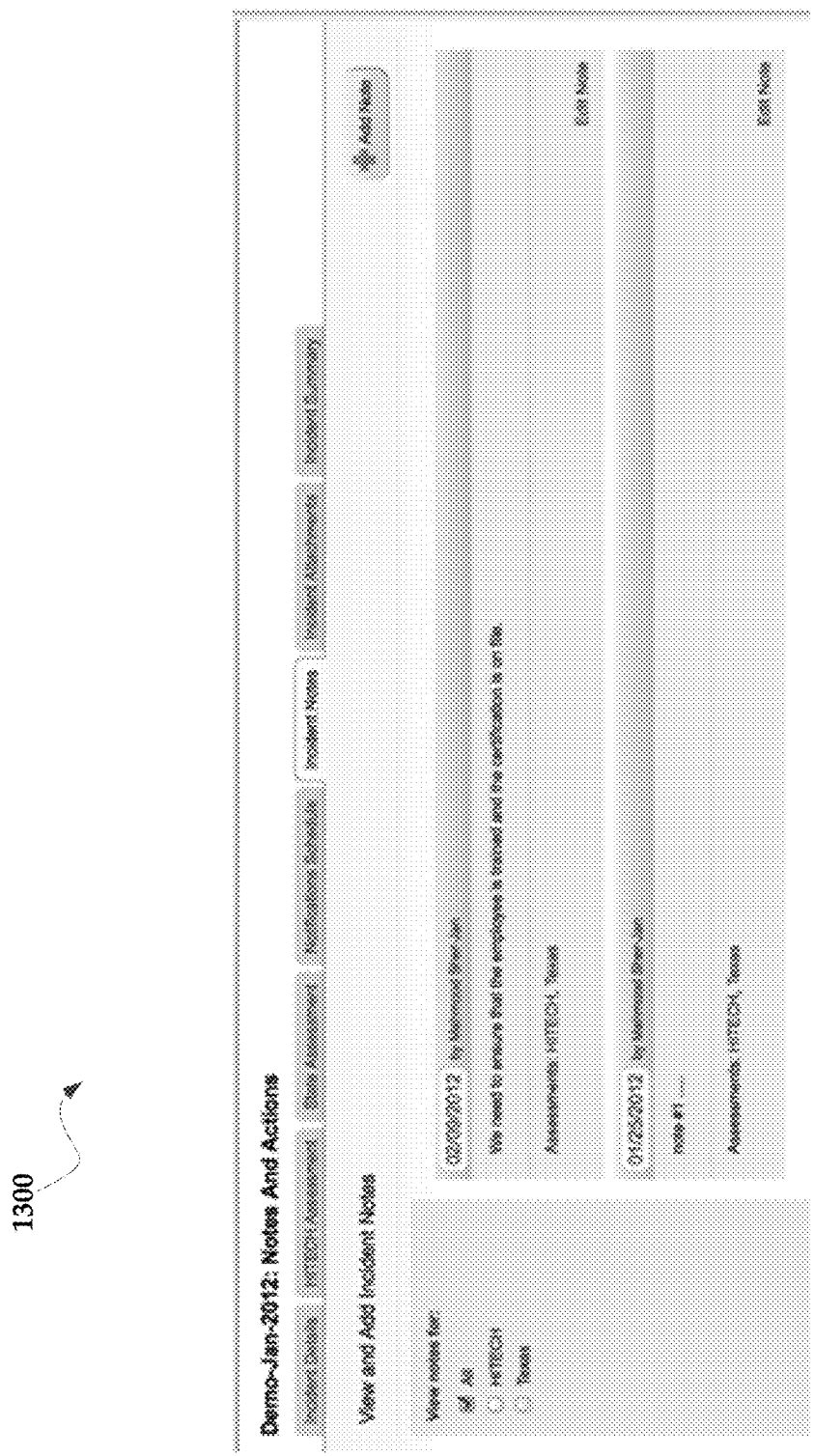

FIGS. 11-13 illustrate exemplary GUIS that are utilized to collect, store, and transmit pertinent documents or data. FIG. 11 illustrates an attachments page 1100 that shows a plurality of documents that have been uploaded to the system such as media notification, attorney general notification, privacy policy, and corrective action plan. Positioned adjacent to the list of documents is a checklist that includes all the pertinent documentation that is to be provided to regulatory authorities, the media, and/or affected individuals. As the required data are uploaded, each required data category is noted with a green check mark. Missing elements can be easily determined and uploaded.

It is noteworthy to mention that the on-time reporting of required incident data may be paramount in determining compliance and good faith on the part of an entrusted entity. Consequently, failure to meet required notification deadlines may result in fines and other regulatory punishment.

FIG. 12 illustrates an upload page 1200 that may be utilized by an entrusted entity to upload and categorize required compliance information (e.g., documents shown in FIG. 11). Files may be tagged with metadata linking them to the related federal and states risk assessments before they are stored in a content repository or transmitted to an appropriate party.

FIG. 13 illustrates an exemplary time stamped notation and actions page 1300 that displays notes entered into the system by a particular end user. Actions may include a note that a particular employee is to be retrained and certified. Any type of related action such as a remedial action, uploading of a file, or other notification and/or compliance related action may be noted and associated with a particular risk assessment.

Figure 14:
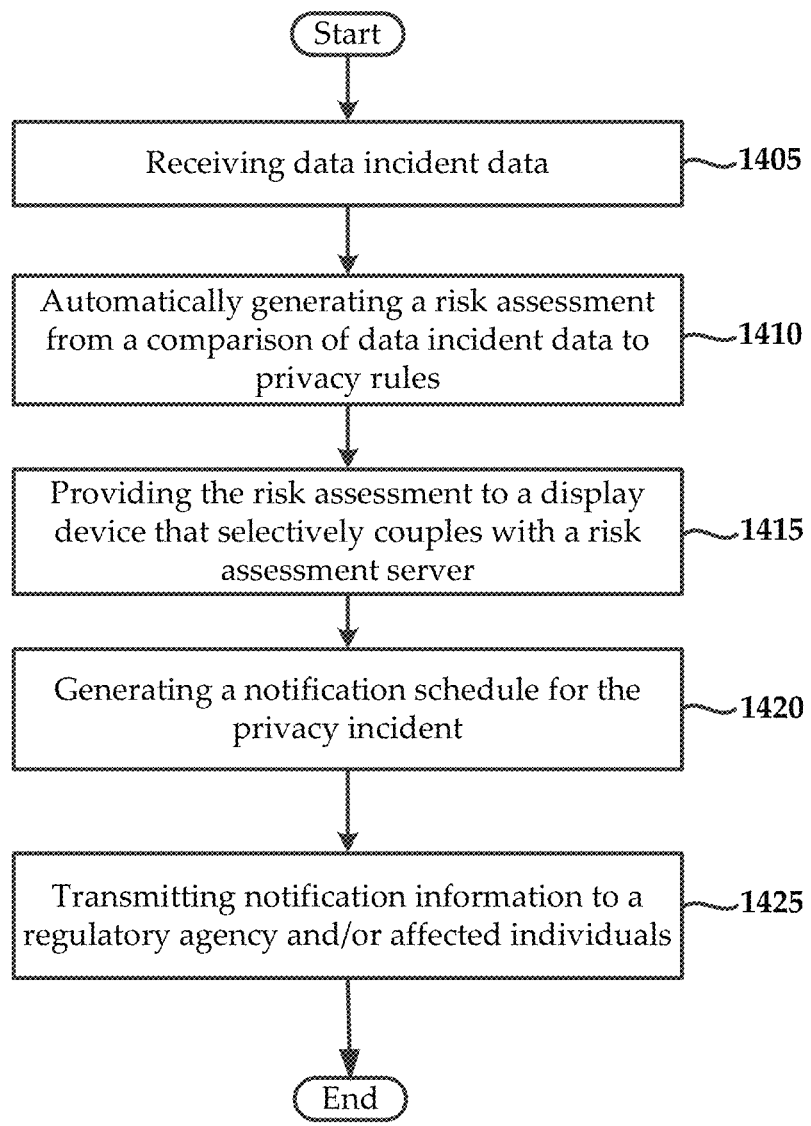
FIG. 14 is a flowchart of an exemplary method for managing a data incident.

FIG. 14 illustrates a flowchart of an exemplary method for managing a data incident. The method may include a step 1405 of receiving data incident data. The data incident data may include information that pertains or corresponds to the data incident. Also, the method may include a step 1410 of automatically generating a risk assessment from a comparison of data incident data to privacy rules. The privacy rules may comprise at least one federal rule and at least one state rule, where each of the rules defining requirements associated with data incident notification laws. Additionally, the comparison may include modeling the data incident data against privacy rules. Also, the method may include a step 1415 of providing the risk assessment to a display device that selectively couples with a risk assessment server. It is noteworthy to mention that the risk assessment may include a visual representation of the risk associated with a data incident relative to the privacy rules.

Additionally, for data incidents that violate a privacy rule (either state or federal) the method may include a step 1420 of generating a notification schedule for the data incident, along with an optional step 1425 of transmitting notification information to a regulatory agency and/or affected individuals (e.g. those who's PII/PHI has been compromised).

Figure 15:
FIG. 15 illustrates an exemplary GUI in the form of a European General Data Privacy Regulation (GDPR) rule risk assessment page.

FIG. 15 illustrates an exemplary GUI in the form of a European General Data Privacy Regulation (GDPR) rule risk assessment page.

Similar to that shown and described in connection with FIG. 7, the exemplary GUI is in the form of a risk assessment page. The risk assessment page includes a heat map and corresponding risk level indicator, which is placed within the heat map. The heat map includes a grid where vertical placement indicates data sensitivity level and horizontal placement indicates severity level.

As is shown, as the sensitivity and severity levels increase, so do the odds that the data incident may trigger an obligation to notify affected parties.

Positioned below the heat map is a notification schedule that includes not only the obligations for the entrusted entity, but also the expected notification dates.

In May of 2018, Europe's General Data Protection Regulation will take effect throughout the European Union. This broad legislation will set data protection standards for the European Union and brings with it large consequences for the trade of information across the Atlantic. Unless the Brexit is completed sooner, the United Kingdom will also be subject to this Regulation. Unlike a Directive, the Regulation will be directly enacted across the European Union without the need for member states to enact their own interpretations.

Of particular concern to businesses that have European Union citizens or residents among their customers or data subjects, is the fact that the GDPR requires reporting of personal data breaches, "where feasible", within 72 hours. Article 33(1). Various exemplary embodiments as described herein allow privacy officers, legal and compliance staff to consistently assess the regulatory risk of data incidents under the GDPR and determine whether and to whom notification is due.

For example, according to many exemplary embodiments, the systems and methods described herein will evaluate:

Whether the data was transmitted electronically, through paper, verbally, or visually;

Exactly what type of device or mode of communication was involved;

What forms of data protection were in place (i.e. redaction, encryption, whether the encryption of NIST standard, passwords, deidentification);

The motives of the party releasing or losing control of the data;

The nature of and relationship to the recipient of the data;

The final disposition of the data (i.e. destroyed, returned, recovered, compromised, accessed, disclosed to Wikileaks, etc.);

Precisely which data elements were involved in the incident, such as:

Government Issued IDs;

Financial account information;

Personal contact information;
Vehicle identification cards;
Information about a person's private life;
Information relating to minors; and
Numerous other categories.

Certain exemplary algorithms assess the multiple factors relating to the incident and provides decision support in the form of risk scores and breach notification guidance that is specific to the requirements of each regulating authority.

European Definitions of "Personal Data."

One difference in approach among jurisdictions is that most state laws in the U.S. refer to "personal information" by codifying the specific data elements that, when used in combination, allow an individual to be identified. The legislative intent behind these laws is to specify how identity may be discerned. European law directly codifies such intent, but leaves the interpretation of the data elements to the reader. For instance, the EU Data Privacy Directive 95/46/EC (the present continental directive that was enacted with some variation in each member country) defines "personal data" as:

"any information relating to an identified or identifiable natural person ("data subject"); an identifiable person is one who can be identified, directly or indirectly, in particular by reference to an identification number or to one or more factors specific to his physical, physiological, mental, economic, cultural or social identity"

In some cases, individual member states have superseded this definition with their own, such as Estonia, which provides an arguably entirely compatible definition, but with some greater specificity, including information concerning the commission of (or falling victim to) an offense, and information on trade union membership.

The definition under the GDPR will be nearly the same, with some important changes that arguably broaden the definition and make clear that the law is not intended to apply to corporations or other entities that are not natural persons:

"any information relating to an identified or identifiable natural person ('data subject'); an identifiable natural person is one who can be identified, directly or indirectly, in particular by reference to an identifier such as a name, an identification number, location data, an online identifier or to one or more factors specific to the physical, physiological, genetic, mental, economic, cultural or social identity of that natural person;"

European Definitions of Data Breach.

How a jurisdiction defines a "breach" is critical to understanding the risk and mitigation factors associated with that jurisdiction.

European Union

The Data Privacy Directive does not provide a definition of breach, but each E.U. member state operates under a definition that is either codified or demonstrated in actual practice. Italy, for example, defines a personal data breach as "a security breach leading, accidentally or not, to the destruction, loss, alteration, unauthorised disclosure of or access to personal data transmitted, stored or otherwise processed in the context of the provision of a publicly available communications service."

The GDPR defines breach as "a breach of security leading to the accidental or unlawful destruction, loss, alteration, unauthorised disclosure of, or access to, personal data transmitted, stored or otherwise processed."

According to exemplary embodiments, the relevant portions of the GDPR, Article 29 Working Party opinions, and other sources of guidance relating to data breach and notification are parsed within the system in order to identify the requirements, exceptions, and factors that affect an organization's regulatory risk with respect to each event or incident that potentially involves personal data.

GDPR's Definition of Personal Data.

As stated above, the GDPR defines personal data as:

"any information relating to an identified or identifiable natural person ('data subject'); an identifiable natural person is one who can be identified, directly or indirectly, in particular by reference to an identifier such as a name, an identification number, location data, an online identifier or to one or more factors specific to the physical, physiological, genetic, mental, economic, cultural or social identity of that natural person." Art 4(1).

Unlike many U.S. state laws that identify which data elements or combination thereof trigger a notification obligation, the GDPR describes the elements more generally and builds them into the definition of personal data as factors that may be used to identify an individual. Among them:

Name;
Identification numbers;
Location data;
Wifi, GPS, Bluetooth, and other location tracking technologies;
Online identifiers;
Usernames that contain identifying information;
Appearance descriptors;
Biometric data;
Genetic information;
DNA analysis results; and/or
Lists of inherited traits.

"Identifiable."

A key term under the GDPR is "identifiable", because it presents a 'moving target' in the context of evolving technology and reasonable efforts to uncover identity. The GDPR's words are carefully chosen to remain relevant over time.

Unlike many US state breach laws, a person's name alone may be sufficiently identifiable as to be considered personal data, and likewise, a collection of other information could make an individual "identifiable" even if the name is not included. As the evolution of technology causes it to be increasingly easy to identify Internet users by using the relation of disparate facts, "identifiable" would seem to be a moving target as the sophistication of technology and the breadth of databases increases.

In the Recitals section, the GDPR states that when determining if a person is identifiable "account should be taken of all the means reasonably likely to be used, such as singling out, either by the controller or by another person to identify the natural person directly or indirectly. To ascertain whether means are reasonably likely to be used to identify the natural person, account should be taken of all objective factors, such as the costs of and the amount of time required for identification, taking into consideration the available technology at the time of the processing and technological developments. The principles of data protection should therefore not apply to anonymous information, namely information which does not relate to an identified or identifiable natural person or to personal data rendered anonymous in such a manner that the data subject is not or no longer identifiable." Recital 26.

"Special Categories" of Personal Data.

The GDPR's Article 9 begins by prohibiting all processing of "personal data revealing racial or ethnic origin, political opinions, religious or philosophical beliefs, or trade-union membership, and the processing of genetic data, biometric data for the purpose of uniquely identifying a natural person, data concerning health or data concerning a natural person's sex life or sexual orientation"

The GDPR provides exceptions to the general prohibition below:

Data subject gives consent. Consent must be unambiguous, given freely, and properly informed. (See also Recital 32)

Personal data was made public by the data subject.

Purposes directly related to employment, social security, and social protection law as authorized by Member State law.

To protect the vital interests of a data subject who is incapable of giving consent.

Processing by a nonprofit, under certain conditions.

Necessary for legal claims.

Necessary for substantial public interest.

For medical diagnosis, under certain conditions.

Necessary for archiving in the public interest (scientific, historical research).

GDPR's Definition of Personal Data Breach.

Under the GDPR, "personal data breach means a breach of security leading to the accidental or unlawful destruction, loss, alteration, unauthorised disclosure of, or access to, personal data transmitted, stored or otherwise processed." Art 4(12).

Using the exemplary systems and methods described herein, data incidents are documented in a record that can be used to comply efficiently with the GDPR's breach notification requirements. The following elements required by the GDPR's Article 33 are tracked by various exemplary embodiments:

A description of the nature of the breach, including:

Categories and approximate number of individuals affected;

Categories and approximate number of records affected;

The name and contact information of the data protection officer or compliance officer to contact for further details; and A description of the measures taken to mitigate the possible adverse effects of the breach.

Figure 16:
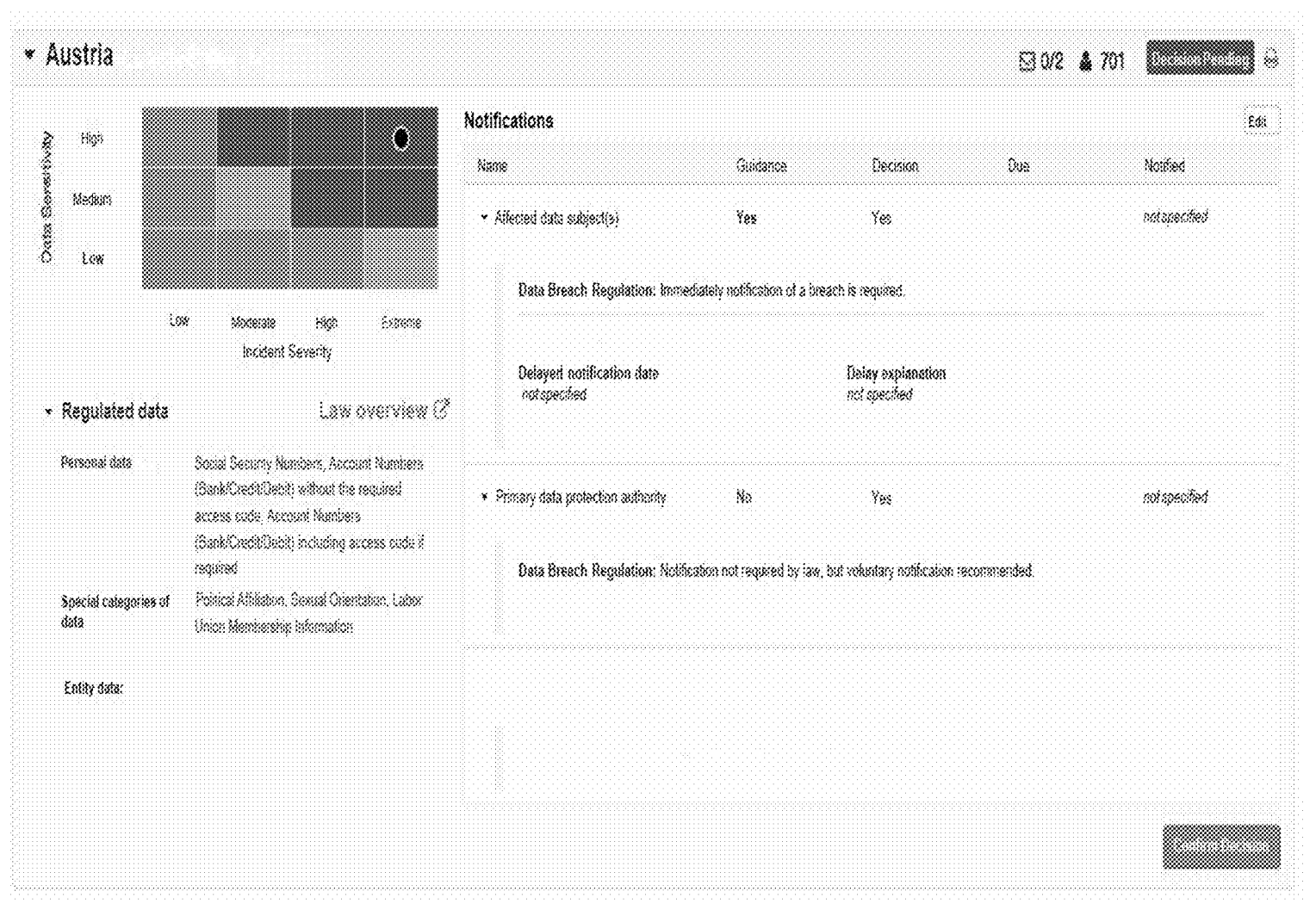

FIG. 16 illustrates an exemplary GUI in the form of a Network and Information Security Directive (NISD) rule risk assessment page of a European Member State.

Similar to that shown and described in connection with FIG. 7, the exemplary GUI is in the form of a risk assessment page. The risk assessment page includes a heat map and corresponding risk level indicator, which is placed within the heat map. The heat map includes a grid where vertical placement indicates data sensitivity level and horizontal placement indicates severity level. As is shown, as the sensitivity and severity levels increase, so do the odds that the data incident may trigger an obligation to notify affected parties.

Positioned below the heat map is a notification schedule that includes not only the obligations for the entrusted entity, but also the expected notification dates.

Europe's new NISD (Network and information Security Directive) will place obligations on Member States to implement additional laws, which include data breach notification rules, also in May 2018.

The NISD is a Directive, rather than a Regulation, so its provisions do not take direct effect upon the people or business entities of Europe. Rather, the Directive obligates Member States to pass laws that conform with its requirements.

The NISD applies to businesses that provide "essential services" such as energy suppliers, airports, banks, utility companies, healthcare providers. It also applies to "digital service providers" such as marketplaces, search engines, and cloud services (but not telecoms).

There are several key differences in scope between the GDPR and the NISD. For instance:

GDPR applies only to "personal data", whereas NISD applies to all forms of data;

GDPR applies to all businesses, whereas NISD applies to operators of "essential services" and "digital service providers" (each as defined); and GDPR personal data breaches must be reported to a data protection authority (DPA), whereas NISD incidents must be reported to a "competent authority" (which may or may not be a DPA, depending upon who is delegated that responsibility by law depending upon the Member State).

There will be breach notification obligations under both the GDPR and the NISD laws. The NISD will require notification by essential services providers "without undue delay," which remains to be interpreted by Member States.

Figure 17:
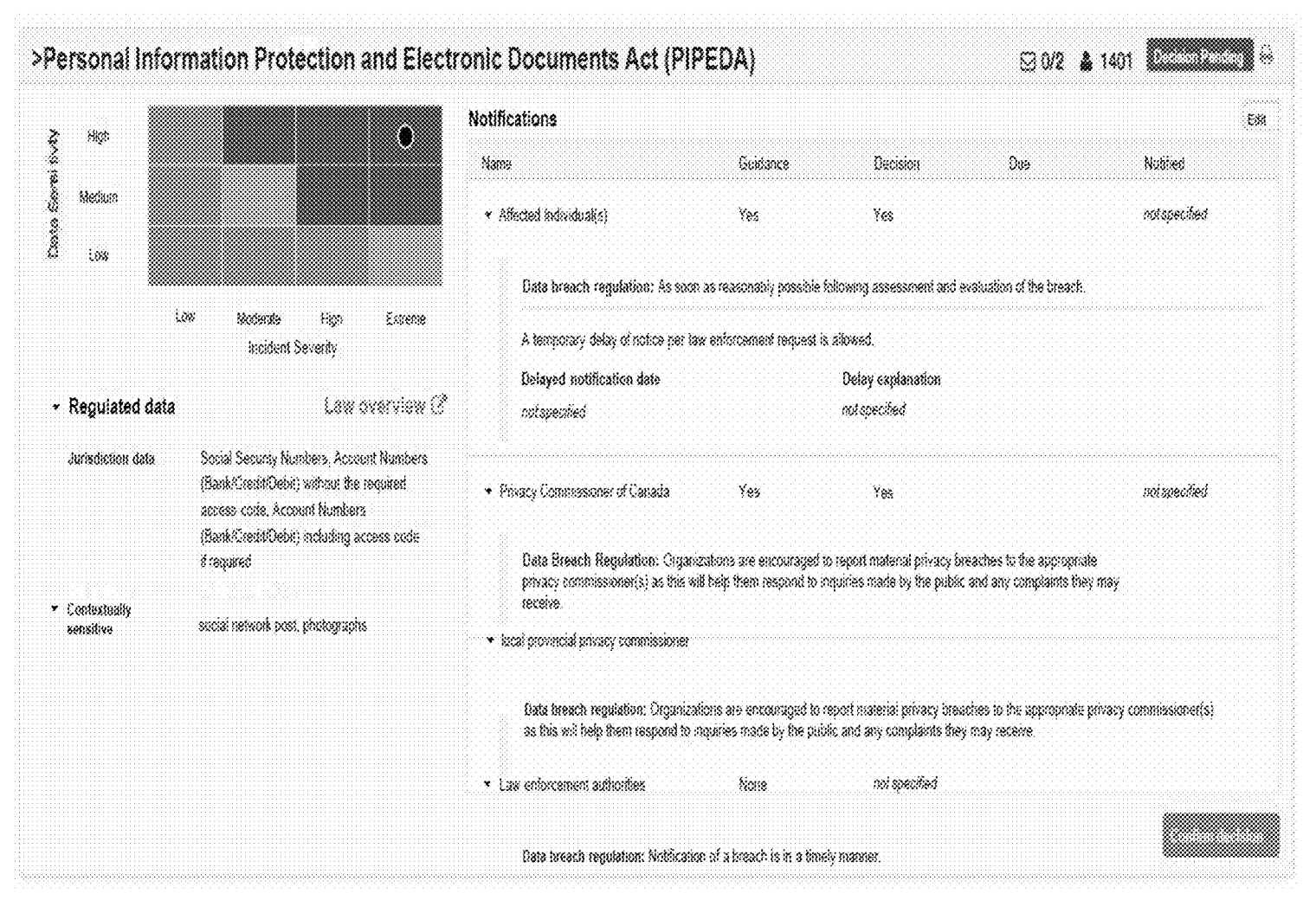

FIG. 17 illustrates an exemplary GUI in the form of a Canadian Personal Information Protection and Electronic Documents Act (PIPEDA) rule risk assessment page.

Similar to that shown and described in connection with FIG. 7, the exemplary GUI is in the form of a risk assessment page. The risk assessment page includes a heat map and corresponding risk level indicator, which is placed within the heat map. The heat map includes a grid where vertical placement indicates data sensitivity level and horizontal placement indicates severity level. As is shown, as the sensitivity and severity levels increase, so do the odds that the data incident may trigger an obligation to notify affected parties.

Positioned below the heat map is a notification schedule that includes not only the obligations for the entrusted entity, but also the expected notification dates.

Canada's federal PIPEDA law, which applies generally to the private sector, chooses a definition for "personal information" that is more like Europe than U.S. state laws, providing simply: "information about an identifiable individual."

Canada's data protection laws that contain data notification obligations are made up of federal laws, provincial laws, and health care sector laws. In general, PIPEDA is the national standard for data protection in the private sector, but in several provinces, the local law is concerned to completely preempt the local legislation because it is "substantially similar." Those provinces are Alberta, British Columbia, Ontario, and Quebec).

In the public sector, the Privacy Act controls. The Privacy Act dates to 1983 and has not been substantially updated since. It does not contain explicit data breach notification obligations.

In both the private and public sectors, provincial health information privacy acts pertain to health information regardless of whether the entity is regulated under private sector laws or public sector laws. There are health information privacy acts in the following provinces: Manitoba, Saskatchewan, Alberta, Ontario, British Columbia, Newfoundland and Labrador, and New Brunswick. Only that of Ontario contains explicit data breach notification obligations.

PIPEDA.

The main private sector privacy law in Canada is the Personal Information Protection and Electronic Documents Act (PIPEDA), effective Jan. 1, 2004. PIPEDA generally applies to organizations involved in commercial activity in all provinces except those that have a substantially similar personal information law (i.e. Alberta, British Columbia, Ontario and Quebec). It also applies to federally-regulated banks and cross-border data transfers across all provinces and territories.

PIPEDA does not apply to:

Federal institutions subject to the Canadian Privacy Act, data collected for household or journalistic purposes, or the name, title, business address, or telephone number of an employee of an organization;

An organization that operates wholly within a province that has legislation that is considered to be substantially similar to PIPEDA (i.e., British Columbia, Québec, Ontario and Alberta), unless the personal information crosses provincial or national borders.

PIPEDA applies to all personal information collected, used or disclosed in the course of commercial activities by all private sector organizations.

PIPEDA does not apply to an organization in respect of the business contact information of an individual that the organization collects, uses or discloses solely for the purpose of communicating or facilitating communication with the individual in relation to their employment, business or profession.

Under PIPEDA, a privacy breach occurs when there is unauthorized access to, or collection, use or disclosure of personal information. A privacy breach may also be a consequence of faulty business procedure or operational break-down.

Personal information under PIPEDA, means information about an identifiable individual.

The Office of the Privacy Commissioner ("OPC") of Canada issued a fact sheet, Complying with the Personal Information Protection and Electronic Documents Act, which further clarifies the meaning of personal information as any factual or subjective information, recorded or not, about an identifiable individual. This includes information in any form, such as:

Age, name, ID numbers, income, ethnic origin, or blood type;

Opinions, evaluations, comments, social status, or disciplinary actions; and

Employee files, credit records, loan records, medical records, existence of a dispute between a consumer and a merchant, intentions (for example, to acquire goods or services, or change jobs).

Personal information does not include the name, title, business address or telephone number of an employee of an organization.

The OPC's guidance provides for the consideration of harm as a condition of notification of affected individuals. Generally, the more sensitive the information, the higher the risk of harm to individuals.

The higher the risk of harm, the more likely the OPC may consider the organization to be under duty to notify the affected individuals, the OPC, and provincial privacy commissioners.

The OPC's Key Steps for Organizations in Responding to Privacy Breaches provides the following guidance for determining harm:

In assessing the possibility of foreseeable harm from the breach, have you considered the reasonable expectations of the individuals? For example, many people would consider a list of magazine subscribers to a niche publication to be potentially more harmful than a list of subscribers to a national newspaper.

Who is the recipient of the information? Is there any relationship between the unauthorized recipients and the data subject? For example, was the disclosure to an unknown party or to a party suspected of being involved in criminal activity where there is a potential risk of misuse? Or was the recipient a trusted, known entity or person that would reasonably be expected to return the information without disclosing or using it?

What harm to the individuals could result from the breach? Examples include:

security risk (e.g., physical safety);

identity theft;

financial loss;

loss of business or employment opportunities; or humiliation, damage to reputation or relationships.

What harm to the organization could result from the breach? Examples include:

loss of trust in the organization;

loss of assets;

financial exposure; or legal proceedings (i.e., class action suits).

What harm could come to the public as a result of notification of the breach? Harm that could result includes:

risk to public health; or risk to public safety.

The OPC provides guidance that is intended to help organizations take the appropriate steps in the event of a privacy breach including notification of affected individuals.

The OPC's Key Steps for Organizations Responding to Privacy Breaches is the source reference for organizations considering whether or not they may be under a duty to notify parties under PIPEDA.

The OPC states that until new provisions dealing with breach reporting, notification and recordkeeping are brought into force, breach reporting will remain voluntary. Until that time, the Office urges organizations to report breaches to the Office by visiting its privacy breaches reporting web page and to notify affected customers where appropriate in accordance with its breach notification guidelines. If you choose not to notify the OPC and it learns of a privacy breach, it may at its discretion open a file to monitor the incident or initiate a complaint investigation.

When deciding whether to notify, the OPC recommends considering the following:

What are the legal and contractual obligations?

What is the risk of harm to the individual?

Is there a reasonable risk of identity theft or fraud (usually because of the type of information lost, such as an individual's name and address together with government-issued identification numbers or date of birth)?

Is there a risk of physical harm (if the loss puts an individual at risk of physical harm, stalking or harassment)?

Is there a risk of humiliation or damage to the individual's reputation (e.g., when the information lost includes mental health, medical or disciplinary records)?

What is the ability of the individual to avoid or mitigate possible harm?

In the event of a breach, the OPC recommends notifying some or all of the following entities.

Affected individuals.

Notification of individuals affected by the breach should occur as soon as reasonably possible following assessment and evaluation of the breach. However, if law enforcement authorities are involved, check with those authorities whether notification should be delayed to ensure that the investigation is not compromised.

Typically, the organization that has a direct relationship with the customer, client or employee should notify the affected individuals, including when the breach occurs at a third party service provider that has been contracted to maintain or process the personal information.

Organizations are encouraged to report material privacy breaches to the appropriate privacy commissioner(s) as this will help them respond to inquiries made by the public and any complaints they may receive. They may also be able to provide advice or guidance to your organization that may be helpful in responding to the breach. The following factors should be considered in deciding whether to report a breach to privacy commissioners' offices:

Any applicable legislation that may require notification;

Whether the personal information is subject to privacy legislation;

The type of the personal information, including whether the disclosed information could be used to commit identity theft; whether there is a reasonable chance of harm from the disclosure, including non-monetary losses;

The number of people affected by the breach;

Whether the individuals affected have been notified; and

If there is a reasonable expectation that the privacy commissioner's office may receive complaints or inquiries about the breach.

Consideration should also be made about whether the following authorities or organizations should also be informed of the breach, as long as such notifications would be in compliance with PIPEDA or similar provincial privacy legislation:

Police.

Notify if theft or other crime is suspected.

Insurers or others.

Notify if required by contractual obligations.

Professional or other regulatory bodies.

Notify if professional or regulatory standards require notification of these bodies.

Credit card companies, financial institutions or credit reporting agencies.

Notify if their assistance is necessary for contacting individuals or assisting with mitigating harm.

Other internal or external parties not already notified.

Third party contractors or other parties who may be impacted.

Internal business units not previously advised of the privacy breach, e.g., government relations, communications and media relations, senior management, etc.; or Union or other employee bargaining units.

The OPC does not provide guidance on specific exceptions to notification, but it does provide guidance as to what factors one should consider when assessing an incident's risk such as encryption and anonymisation. Exceptions may be specified when provisions related to breach notification come into force under the Digital Privacy Act.

The content of notifications will vary depending on the particular breach and the method of notification chosen. Notifications should include, as appropriate:

Information about the incident and its timing in general terms;

A description of the personal information involved in the breach;

A general account of what the organization has done to control or reduce the harm;

What the organization will do to assist individuals and what steps the individual can take to avoid or reduce the risk of harm or to further protect themselves. Possible actions include arranging for credit monitoring or other fraud prevention tools, providing information on how to change a social insurance number (SIN), personal health card or driver's license number.

The preferred method of notification is direct—by phone, letter, email or in person—to affected individuals. Indirect notification—website information, posted notices, media—should generally only occur where direct notification could cause further harm, is prohibitive in cost or the contact information for affected individuals is not known. Using multiple methods of notification in certain cases may be appropriate. One should also consider whether the method of notification might increase the risk of harm.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A method for managing a data incident, comprising:

receiving, via a risk assessment server, in response to an occurrence of the data incident, data incident data that comprises information corresponding to the data incident, the data incident further comprising intentional or unintentional compromise, disclosure or release of personal data or personally identifiable information to an untrusted or unauthorized environment;

automatically generating, via the risk assessment server, a risk assessment and decision-support guidance whether the data incident is reportable from a comparison of the data incident data to privacy rules, the privacy rules comprising at least one European General Data Privacy Regulation (GDPR) rule, each rule defining requirements associated with data incident notification obligations;

generating a risk assessment guidance interface when the comparison indicates that the data incident violates at least one of the privacy rules;

wherein the risk assessment guidance interface comprises an impact summary that indicates which of the privacy rules was violated and one or more entities implicated or impacted in the data incident; and wherein the receiving data incident data further comprises: providing, in response to a determination of a violation of at least one of the privacy rules, one or more questions to a display device that elicits information corresponding to the data incident, the one or more questions tailored to specific criteria of the at least one of the privacy rules; and receiving responses to the one or more questions; and generating a notification schedule when the comparison indicates that the data incident violates and triggers a notification obligation according to the at least one European General Data Privacy Regulation (GDPR) rule; and wherein the notification schedule comprises notification dates that are based upon a violated European General Data Privacy Regulation (GDPR) rule, along with notification requirements that describe information that is to be provided to a regulatory agency or to an affected individual whose personal data has been compromised, disclosed or released as a result of the data incident.

2. The method according to claim 1, wherein receiving data incident data comprises:
providing one or more data incident risk factor questions to the display device that elicit information corresponding to the data incident; and
receiving responses to the one or more data incident risk factor questions.

3. The method according to claim 1, wherein the at least one European General Data Privacy Regulation (GDPR) rule governs privacy breaches relative to at least one of personal data, special categories of personal data, or combinations thereof.

4. The method according to claim 1, wherein the risk assessment comprises a risk level that indicates severity of the data incident relative to the at least one European General Data Privacy Regulation (GDPR) rule.

5. The method according to claim 4, wherein the risk level is associated with a color, wherein a hue of the color is associated with the severity of the data incident and a sensitivity of the data incident data as determined by the comparison.

6. The method according to claim 1, wherein the risk assessment defines one or more exceptions that apply to at least a portion of the data incident data based upon the comparison.

7. The method according to claim 1, wherein the risk assessment comprises at least a portion of the at least one European General Data Privacy Regulation (GDPR) rule.

8. The method according to claim 1, further comprising providing an alert to the display device when the comparison indicates that the data incident violates and triggers a notification obligation according to the at least one European General Data Privacy Regulation (GDPR) rule.

9. The method according to claim 1, further comprising receiving the information that is to be provided to a regulatory agency and storing the same in a content repository associated with the risk assessment server.

10. The method according to claim 1, wherein comparison includes modeling of the data incident data to the privacy rules to determine a severity and a data sensitivity of the data incident.

11. The method according to claim 1, wherein the comparison comprises:
modeling the data incident data to determine severity and data sensitivity of the data incident by evaluating the data incident data relative to the at least one European General Data Privacy Regulation (GDPR) rule; and
generating a risk assessment from the modeling.

12. The method according to claim 1, further comprising generating a risk assessment guidance interface when the comparison indicates that the data incident violates the at least one European General Data Privacy Regulation (GDPR) rule.

13. The method according to claim 1, the privacy rules further comprising at least one Network and Information Security Directive (NISD) rule of a European Member State.

14. A risk assessment server for managing a data incident, the server comprising:
a memory for storing executable instructions;
a processor for executing the instructions;
input circuitry stored in memory and executable by the processor to receive in response to an occurrence of the data incident, data incident data, the data incident data comprising information corresponding to the data incident, the data incident further comprising intentional or unintentional compromise, disclosure or release of personal data, personally identifiable information, or protected health information to an untrusted or unauthorized environment;
risk assessment circuitry stored in memory and executable by the processor to generate a risk assessment from a comparison of the
data incident data to privacy rules, the privacy rules comprising
at least one European General Data Privacy Regulation (GDPR) rule, each of the rules defining requirements associated with data incident notification laws;
user interface circuitry stored in memory and executable by the processor to provide the risk assessment to a display device that selectively couples with the risk assessment server; and wherein the receiving data incident data further comprises: providing, in response to a determination of at least one of the privacy rules, one or more questions to the display device that elicits information corresponding to the data incident, the one or more questions tailored to specific criteria of the at least one of the privacy rules; and receiving responses to the one or more questions;
notification circuitry stored in memory and executable by the processor to generate a notification schedule when the comparison indicates that the data incident violates and triggers a notification obligation according to the at least one European General Data Privacy Regulation (GDPR) rule; and wherein the notification schedule comprises notification dates that are based upon a violated European General Data Privacy Regulation (GDPR) rule, along with notification requirements that describe information that is to be provided to a regulatory agency or to an affected individual whose personal data has been compromised, disclosed or released as a result of the data incident.

15. The server according to claim 14, wherein the input circuitry further:
generates one or more questions to the display device that elicit data incident data corresponding to the data incident;
receives responses to the one or more questions;
generates a summary of responses to the one or more questions;
provides the summary to the display device; and
receives confirmation of the summary.

16. The server according to claim 14, wherein the risk assessment circuitry generates a risk assessment that comprises a risk level that indicates a severity of the data incident relative to at least one of at least one federal rule, at least one state rule, or the at least one European General Data Privacy Regulation (GDPR) rule or combinations thereof.

17. The server according to claim 14, wherein the risk assessment circuitry creates a notification that one or more exceptions apply to at least a portion of the data incident data based upon modeling.

18. The server according to claim 14, further comprising reporting circuitry stored in memory and executable by the processor to receive the information that is to be provided to the regulatory agency and an affected individual and stores the same in a content repository associated with the risk assessment server.

19. The server according to claim 14, the privacy rules further comprising at least one rule under Canada's Personal Information Protection and Electronic Documents Act (PIPEDA).

* * * * *